(12) United States Patent
Sun et al.

(10) Patent No.: US 10,828,391 B2
(45) Date of Patent: *Nov. 10, 2020

(54) REGENERATIVE MATERIALS

(71) Applicant: LifeCell Corporation, Branchburg, NJ (US)

(72) Inventors: Wenquan Sun, Warrington, PA (US); Melissa Richter Bowley, Newport, RI (US); Raghav Goel, Plymouth, MN (US)

(73) Assignee: LifeCell Corporation, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,848

(22) Filed: May 27, 2016

(65) Prior Publication Data

US 2016/0271295 A1 Sep. 22, 2016

Related U.S. Application Data

(63) Continuation of application No. 13/446,422, filed on Apr. 13, 2012, now Pat. No. 9,375,513.

(60) Provisional application No. 61/475,378, filed on Apr. 14, 2011.

(51) Int. Cl.

| | |
|---|---|
| *A61L 15/42* | (2006.01) |
| *A61L 15/44* | (2006.01) |
| *A61L 27/56* | (2006.01) |
| *A61L 27/24* | (2006.01) |
| *A61L 27/20* | (2006.01) |
| *A61L 27/26* | (2006.01) |
| *A61L 27/36* | (2006.01) |
| *A61L 27/38* | (2006.01) |
| *A61L 27/54* | (2006.01) |
| *A61K 38/18* | (2006.01) |
| *A61K 38/19* | (2006.01) |
| *A61K 35/35* | (2015.01) |
| *A61K 35/545* | (2015.01) |
| *A61F 2/02* | (2006.01) |
| *A61L 2/08* | (2006.01) |
| *A61L 2/20* | (2006.01) |

(52) U.S. Cl.

CPC ............... *A61L 27/24* (2013.01); *A61F 2/02* (2013.01); *A61K 35/35* (2013.01); *A61K 35/545* (2013.01); *A61K 38/18* (2013.01); *A61K 38/19* (2013.01); *A61L 27/20* (2013.01); *A61L 27/26* (2013.01); *A61L 27/362* (2013.01); *A61L 27/3687* (2013.01); *A61L 27/3691* (2013.01); *A61L 27/3834* (2013.01); *A61L 27/54* (2013.01); *A61L 27/56* (2013.01); *A61L 2/081* (2013.01); *A61L 2/087* (2013.01); *A61L 2/206* (2013.01); *A61L 2430/34* (2013.01)

(58) Field of Classification Search
CPC ......... A61F 2/2418; A61F 2013/53782; A61L 15/425; A61L 2300/404; A61L 27/56; A61L 2430/34; A61L 15/44

See application file for complete search history.

(56) References Cited

U.S. PATENT DOCUMENTS

| | | |
|---|---|---|
| 4,582,640 A | 4/1986 | Smestad et al. |
| 4,902,508 A | 2/1990 | Badylak et al. |
| 4,969,912 A | 11/1990 | Kelman et al. |
| 5,024,841 A | 6/1991 | Chu et al. |
| 5,104,957 A | 4/1992 | Kelman et al. |
| 5,131,850 A | 7/1992 | Brockbank |
| 5,160,313 A | 11/1992 | Carpenter et al. |
| 5,231,169 A | 7/1993 | Constantz et al. |
| 5,254,133 A | 10/1993 | Seid |
| 5,275,826 A | 1/1994 | Badylak et al. |
| 5,284,655 A | 2/1994 | Bogdansky et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,489,304 A | 2/1996 | Orgill et al. |
| 5,613,982 A | 3/1997 | Goldstein |
| 5,622,867 A | 4/1997 | Livesey et al. |
| 5,632,778 A | 5/1997 | Goldstein |
| 5,641,518 A | 6/1997 | Badylak et al. |
| 5,728,752 A | 3/1998 | Scopelianos et al. |
| 5,739,176 A | 4/1998 | Dunn et al. |
| 6,027,743 A | 2/2000 | Khouri et al. |
| 6,096,347 A | 8/2000 | Geddes et al. |
| 6,179,872 B1 | 1/2001 | Bell et al. |
| 6,194,136 B1 | 2/2001 | Livesey et al. |
| 6,326,018 B1 | 12/2001 | Gertzman et al. |
| 6,371,992 B1 | 4/2002 | Tanagho et al. |
| 6,432,710 B1 | 8/2002 | Boss, Jr. et al. |

(Continued)

FOREIGN PATENT DOCUMENTS

| | | |
|---|---|---|
| EP | 1683417 A1 | 7/2006 |
| EP | 1433423 B1 | 12/2008 |

(Continued)

OTHER PUBLICATIONS

Ducksters. Chemical Mixtures. Date retrieved: Nov. 16, 2017. <http://www.ducksters.com/science/chemistry/chemical_mixtures.php>. (Year: 2017).*

(Continued)

*Primary Examiner* — Tracy Liu

(74) *Attorney, Agent, or Firm* — McCarter & English, LLP

(57) ABSTRACT

Methods of making tissue fillers are provided. In certain embodiments, the tissue is flake-like and has regenerative properties.

23 Claims, 14 Drawing Sheets

(56) References Cited

U.S. PATENT DOCUMENTS

| | | | |
|---|---|---|---|
| 6,485,723 | B1 | 11/2002 | Badylak et al. |
| 6,576,265 | B1 | 6/2003 | Spievack |
| 6,599,318 | B1 | 7/2003 | Gabbay |
| 6,613,278 | B1 | 9/2003 | Mills et al. |
| 6,666,892 | B2 | 12/2003 | Hiles et al. |
| 6,933,326 | B1 | 8/2005 | Griffey et al. |
| 7,358,284 | B2 | 4/2008 | Griffey et al. |
| 7,425,322 | B2 | 9/2008 | Cohn et al. |
| 7,498,040 | B2 | 3/2009 | Masinaei et al. |
| 7,498,041 | B2 | 3/2009 | Masinaei et al. |
| 7,799,767 | B2 | 9/2010 | Lamberti et al. |
| 7,838,021 | B2 | 11/2010 | Lafont et al. |
| 8,067,149 | B2 | 11/2011 | Livesey et al. |
| 8,324,449 | B2 | 12/2012 | McQuillan et al. |
| 2002/0103542 | A1 | 8/2002 | Bilbo |
| 2003/0035843 | A1 | 2/2003 | Livesey et al. |
| 2003/0039678 | A1 | 2/2003 | Stone et al. |
| 2003/0143207 | A1 | 7/2003 | Livesey et al. |
| 2004/0037735 | A1 | 2/2004 | DePaula et al. |
| 2004/0078077 | A1 | 4/2004 | Binette et al. |
| 2005/0028228 | A1 | 2/2005 | McQuillan et al. |
| 2005/0125077 | A1 | 6/2005 | Harmon et al. |
| 2005/0159822 | A1 | 7/2005 | Griffey et al. |
| 2006/0058892 | A1 | 3/2006 | Lesh et al. |
| 2006/0073592 | A1 | 4/2006 | Sun et al. |
| 2006/0210960 | A1 | 9/2006 | Livesey et al. |
| 2007/0071729 | A1 | 3/2007 | Bernstein |
| 2007/0078522 | A2 | 4/2007 | Griffey et al. |
| 2007/0104759 | A1 | 5/2007 | Dunn et al. |
| 2007/0248575 | A1 | 10/2007 | Connor et al. |
| 2008/0027542 | A1 | 1/2008 | McQuillan et al. |
| 2008/0027562 | A1 | 1/2008 | Fujisato et al. |
| 2008/0279824 | A1 | 11/2008 | Matheny et al. |
| 2009/0024224 | A1* | 1/2009 | Chen .......... A61B 17/1604 623/23.72 |
| 2009/0035289 | A1 | 2/2009 | Wagner et al. |
| 2009/0306790 | A1 | 12/2009 | Sun |
| 2010/0021961 | A1 | 1/2010 | Fujisato et al. |
| 2010/0040687 | A1 | 2/2010 | Pedrozo et al. |
| 2010/0058952 | A1 | 3/2010 | Yang et al. |
| 2010/0209408 | A1 | 8/2010 | Stephen et al. |
| 2010/0272782 | A1 | 10/2010 | Owens et al. |
| 2011/0020271 | A1 | 1/2011 | Niklason et al. |
| 2012/0010728 | A1 | 1/2012 | Sun et al. |
| 2012/0040013 | A1 | 2/2012 | Owens et al. |
| 2012/0263763 | A1 | 10/2012 | Sun et al. |
| 2013/0053960 | A1 | 2/2013 | Park et al. |
| 2013/0121970 | A1 | 5/2013 | Owens et al. |
| 2013/0158676 | A1 | 6/2013 | Hayzlett et al. |

FOREIGN PATENT DOCUMENTS

| | | | |
|---|---|---|---|
| WO | 1998/44809 A1 | 10/1998 | |
| WO | WO-1999/32049 A1 | 7/1999 | |
| WO | WO-1999/65470 A1 | 12/1999 | |
| WO | WO-2000/016822 A1 | 3/2000 | |
| WO | WO-2000/047114 A1 | 8/2000 | |
| WO | WO-2003/017826 A2 | 3/2003 | |
| WO | WO-2003/032735 A1 | 4/2003 | |
| WO | WO-2005/009134 A1 | 2/2005 | |
| WO | 2005/120597 A1 | 12/2005 | |
| WO | WO-2007/043513 A1 | 4/2007 | |
| WO | WO-2007/134134 A2 | 11/2007 | |
| WO | WO-2008134305 A2 * | 11/2008 | ......... A61L 27/3604 |
| WO | WO-2009/009620 A2 | 1/2009 | |
| WO | WO-2010/019753 A2 | 2/2010 | |
| WO | WO-2010/078353 A2 | 7/2010 | |
| WO | WO-2012/142419 A1 | 10/2012 | |
| WO | WO-2012/166784 A1 | 12/2012 | |

OTHER PUBLICATIONS

Ahn et al., "The past, present, and future of xenotransplantation" *Yonsei Med J.*, 45(6)1017-1024 (Dec. 31, 2004).

Allman et al., "Xenogeneic Extracellular Matrix Grafts Elicit a TH2-Restricted Immune Response" *Transplantation*, 71(11):1631-1640 (Jun. 15, 2001).

Aycock et al., "Parastomal Hernia Repair With Acellular Dermal Matrix" *J. Wound Ostomy Continence Nurs.*, 34(5):521-523 (2007).

Badylak et al., "Endothelial cell adherence to small intestinal submucosa: An acellular bioscaffold" *Biomaterials*, 20:2257-2263 (1999).

Badylak et al., "Extracellular Matrix as a Biological Scaffold Material: Structure and Function" *Acta Biomaterialia*, 5(1):1-13 (2009).

Beniker et al., "The use of acellular dermal matrix as a scaffold for periosteum replacement" *Orthopedics*, 26(5 Suppl):s591-s596 (May 2003).

Bruder et al., "The Effect of Implants Loaded with Autologous Mesenchymal Stem Cells on the Healing of Canine Segmental Bone Defects" *J. Bone Joint Surg.*, 80:985-986 (1998).

Buma et al., "Tissue engineering of the meniscus" *Biomaterials*, 25(9):1523-1532 (2004).

Chaplin et al., "Use of an Acellular Dermal Allograft for Dural Replacement: An Experimental Study" *Neurosurgery*, 45(2):320-327 (Aug. 1999).

Chen et al. "Acellular Collagen Matrix as a Possible 'Off the Shelf' Biomaterial for Urethral Repair" *Urology*, 54(3):407-410 (1999).

Collins et al., "Cardiac xenografts between primate species provide evidence for the importance of the α-galactosyl determinant in hyperacute rejection" *J. Immunol.*, 154:5500-5510 (1995).

Costantino et al., "Human Dural Replacement With Acellular Dermis: Clinical Results and a Review of the Literature" *Head & Neck*, 22:765-771 (Dec. 2000).

Dobrin et al., "Elastase, collagenase, and the biaxial elastic properties of dog carotid artery" *Am. J. Physiol. Heart Circ. Physiol.*, 247:H124-H131 (1984).

Edel, "The use of a connective tissue graft for closure over an immediate implant covered with occlusive membrane" *Clin. Oral Implants Res.*, 6:60-65 (1995) (Abstract).

Fowler et al., "Ridge Preservation Utilizing an Acellular Dermal Allograft and Demineralized Freeze-Dried Bone Allograft: Part II. Immediate Endosseous Impact Placement" *J. Periodontol.*, 71:1360-1364 (2000).

Fowler et al., "Root Coverage with an Acellular Dermal Allograft: A Three-Month Case Report" *J. Contemp. Dental Pract.*, 1(3):1-8 (2000).

Galili et al., "Man, Apes, and Old World Monkeys Differ from Other Mammals in the Expression of α-Galactosyl Epitopes on Nucleated Cells" *J. Biol. Chem.*, 263(33):17755-17762 (1988).

Galili et al., "Interaction Between Human Natural Anti-α-Galactosyl Immunoglobulin G and Bacteria of the Human Flora" *Infect. Immun.*, 56(7):1730-1737 (1988).

Galili et al., "Interaction of the Natural Anti-Gal Antibody with α-Galactosyl Epitopes: a Major Obstacle for Xenotransplantation in Humans" *Immunology Today*, 14(10):480-482 (1993).

Gamba et al. "Experimental abdominal wall defect repaired with acellular matrix" *Pediatr. Surg. Int.*, 18:327-331 (2002).

Gebhart et al., "A radiographical and biomechanical study of demineralized bone matrix implanted into a bone defect of rat femurs with and without bone marrow" *Acta Orthop. Belg.*, 57(2):130-143 (1991) (Abstract).

Hammond et al., "Parastomal Hernia Prevention Using a Novel Collagen Implant: A Randomised Controlled Phase 1 Study" *Hernia*, 12:475-481 (2008).

Kay et al., "Guided Bone Regeneration: Integration of a Resorbable Membrane and a Bone Graft Material," *Pract. Periodontics Aesthet Dent.*, vol. 9(2):185-94 (1996).

Kish et al., "Acellular Dermal Matrix (AlloDerm): New Material in the Repair of Stoma Site Hernias" *The American Surgeon*, 71:1047-1050 (Dec. 2005).

Kridel et al., "Septal Perforation Repair with Acellular Human Dermal Allograft" *Arch. Otolaryngol. Head Neck Surg.*, 124:73-78 (Jan. 1998).

Laidlaw et al., "Tympanic Membrane Repair With a Dermal Allograft" *Laryngoscope*, 111:702-707 (Apr. 2001).

(56) References Cited

OTHER PUBLICATIONS

Lee et al., "In vitro evaluation of a poly(lactide-co-glycolide)-collagen composite scaffold for bone regeneration" *Biomaterials*, 27:3466-3472 (2006).

Lu et al., "Novel Porous Aortic Elastin and Collagen Scaffolds for Tissue Engineering" *Biomaterials*, 25(22):5227-5237 (2004).

Marzaro et al., "Autologous satellite cell seeding improves in vivo biocompatibility of homologous muscle acellular matrix implants," Int. J. Mol. Med. 10:177-182 (2002).

Office Action dated Jan. 29, 2014 issued in U.S. Appl. No. 13/717,828, filed Dec. 18, 2012.

Parnigotto et al., "Experimental Defect in Rabbit Urethra Repaired with Acellular Aortic Matrix," Urolog. Res. 28(1):46-51.

Reddy et al., "Regeneration of Functional Bladder Substitutes Using Large Segment Acellular Matrix Allografts in a Porcine Model," J. Urol. 164:936-941 (2000).

Simon et al., "Early failure of the tissue engineered porcine heart valve Synergraft™ in pediatric patients" *Eur. J. Cardiothorac. Surg.*, 23(6):1002-1006 (2003).

Suckow et al., "Enhanced Bone Regeneration Using Porcine Small Intestine Submucosa," *J. Invest. Surg.*, vol. 12(5):277-87 (1999).

Zheng et al. "Porcine small intestine submucosa (SIS) is not an acellular collagenous matrix and contains porcine DNA: Possible implications in human implantation" *J. Biomed. Mater. Res. B: Appl. Biomater.*, 73(1):61-67 (2005).

Zhao et al., "The Study of the Feasibility of Segmental Bone Defect Repair with Tissue-Engineered Bone Membrane: a Qualitative Observation," *Strat. Traum. Limb Recon.*, vol. 3: 57-64 (2008).

"Methods and Techniques for Frozen Tissue Sections" IHC World, retrieved from Internet <URL: <http://web.archive.org/web/20101007213437/http://ihcworld.com/_protocols/histology/frozen_section.htm>>, 1 page, published Oct. 7, 2010, last accessed on Sep. 15, 2015.

Ducksters, Chemical Mixtures, Date retrieved: Nov. 10, 2015, <http://www.ducksters.com/science/chemistry/chemical_mixtures.php>.

BCbioLibrary, Sectioning of OCT Embedded Tissue, (2008), http://www.bcbiolibrary.icapture.ubc.ca/pathologists-researchers/docs/BL.LAB.GN.002.01%20Sectioning%20of%20OCT%20Embedded%20Tissue.pdf, p. 4.

\* cited by examiner

5cm x 5cm
3mm THICK

4 WEEKS, 40X

4 WEEKS, 100X

8 WEEKS, 100X

8 WEEKS, 40X

REGENERATIVE MATERIALS

This application is a continuation of U.S. application Ser. No. 13/446,422, filed Apr. 13, 2012 which claims priority under 35 U.S.C. § 119 to U.S. Provisional Application No. 61/475,378, which was filed on Apr. 14, 2011.

The present disclosure relates to tissue fillers, and more particularly, to methods of preparing tissue fillers having a flake-like shape and tissue fillers prepared according to those methods.

Various types of wound dressings and soft tissue fillers are used to regenerate, repair, or otherwise treat diseased or damaged tissues and organs. Such materials include hyaluronan-based gels, solubilized and cross-linked collagen compositions, micronized tissue matrices, and synthetic polymeric compositions in hydrogel or other forms. Each of these materials has potential drawbacks if used as bulk soft tissue fillers or deep wound dressings, including limited suitability for deep wounds, inability to regenerate, tendency to increase inflammatory response, or tendency to degrade upon exposure to radiation.

According to certain embodiments, a method for preparing a tissue matrix composition is provided. The method comprises selecting a collagen-based tissue matrix, contacting the matrix with a cryoprotectant solution, freezing the matrix, and cutting the matrix, wherein the temperature of the tissue matrix ranges from −10° C. to −40° C. for the cutting step.

In certain embodiments, a tissue matrix composition is provided. The composition comprises a collagen-based tissue matrix, wherein the matrix has been contacted with a cryoprotectant solution and frozen thereafter, and wherein the matrix has been cut at a temperature between −10° C. and −40° C. after freezing.

In certain embodiments, a tissue matrix composition is provided. The composition comprises a collagen-based tissue matrix, wherein the tissue matrix comprises tissue particles having a size distribution ranging from 0.2-5 mm in length, 0.203 mm in width, and 0.02-0.3 mm in thickness.

In certain embodiments, a method for preparing a tissue matrix composition is provided. The method comprises selecting a collagen-based matrix, contacting the matrix with a cryoprotectant solution, freezing the matrix, adjusting the temperature of the tissue matrix and the cryoprotectant to between −10° C. to −40° C., cutting the frozen tissue matrix, placing the cut tissue matrix in a liquid to form a suspension, and freeze-drying the suspension.

DESCRIPTION OF CERTAIN EXEMPLARY EMBODIMENTS

Figure 1:
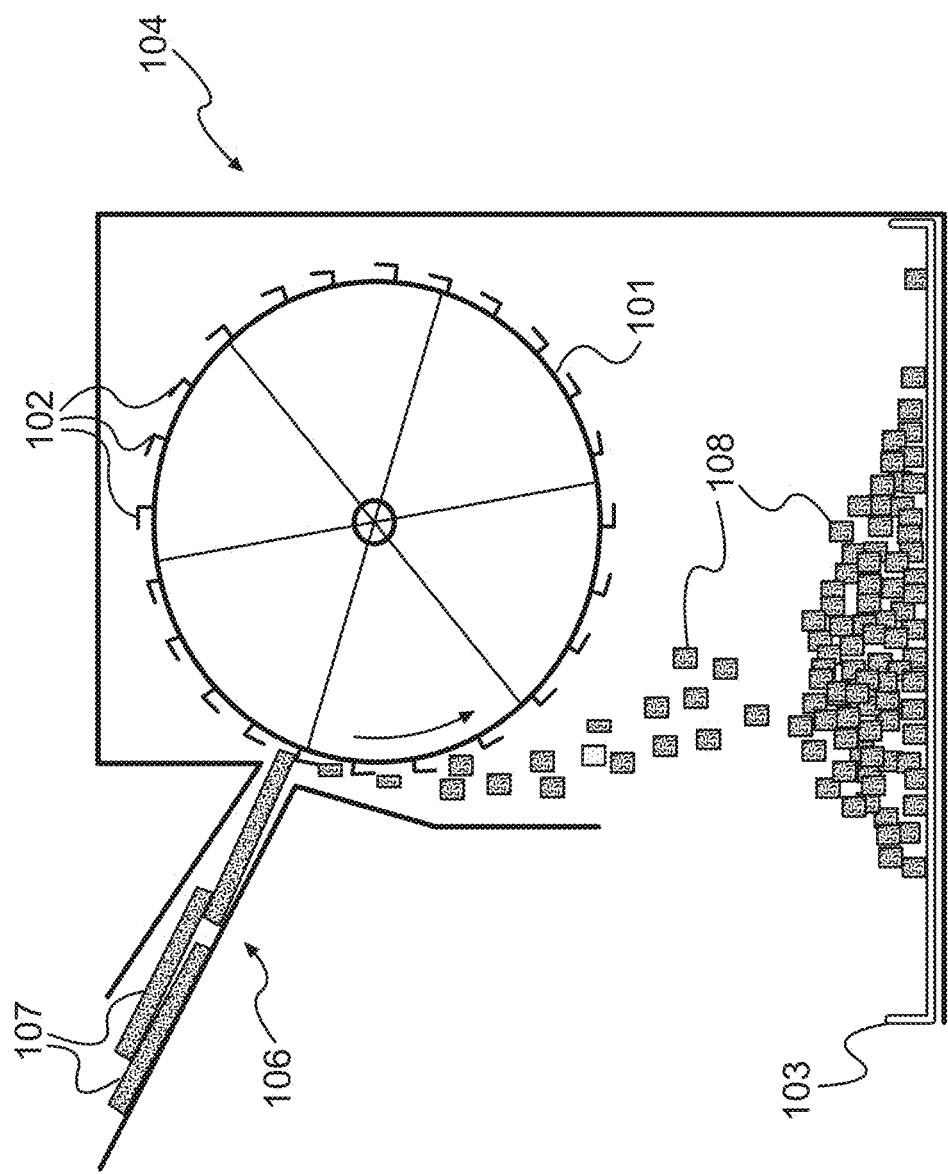
FIG. 1 is a diagram of a grating device for performing methods of the present disclosure, according to certain embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints. It will be understood that the benefits and advantages described above may relate to one embodiment or may relate to several embodiments. Where appropriate, aspects of any of the examples and embodiments described above may be combined with aspects of any of the other examples described to form further examples having comparable or different properties and addressing the same or different problems.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein, "tissue matrix" will refer to material derived from animal tissue that includes a collagen-containing matrix. Such tissue matrices can include intact tissues, tissues that have been partially or completely decellularized, or synthetic collagenous matrices (e.g., 3-D matrices formed from suspended or otherwise processed tissues). As described further below, suitable tissue matrices can be acellular. Any suitable tissue matrix can be used, depending on the intended implantation site, so long as the tissue is amenable for use with the methods described herein.

The cut tissue matrix, such as the flake-like tissue matrix disclosed herein, possesses several properties that make it suitable to use as a bulk soft tissue filler or deep wound dressing. The flake-like tissue matrix is regenerative, permitting host cell repopulation and revascularization. The large size of the individual tissue flakes, relative to micronized tissue particles, prevents the undesirable migration of the flakes into the areas surrounding the original treatment site. The flake-like tissue matrix disclosed herein has been found to be more stable and resistant to enzymatic degradation when compared to micronized tissue particles. The size and/or geometry of the tissue flakes allows them to form a stable suspension without gelling or phase separation, which makes the tissue fillers suitable for filling large voids (tens to hundreds of milliliters). When used to form a suspension that can be freeze-dried, the suspension of tissue flakes can contain relatively large, inter-connected channels that permit fluids to flow freely. When used as wound dressings and/or with negative-pressure wound therapy systems, the channels can help support host cell repopulation and revascularization. These inter-connected channels can transduce pressure, making the flake-like tissue matrix more amenable for the treatment of deep wounds, while also being compatible with negative pressure therapy.

According to certain embodiments, a method for preparing a tissue matrix composition is provided. The method comprises selecting a collagen-based tissue matrix, contacting the matrix with a cryoprotectant solution, freezing the matrix, and cutting the matrix, wherein the temperature of the tissue matrix ranges from −10° C. to −40° C. for the cutting step. In certain embodiments, an additional method for preparing a tissue matrix composition is provided. The method comprises selecting a collagen-based matrix, contacting the matrix with a cryoprotectant solution, freezing the matrix, adjusting the temperature of the tissue matrix and the cryoprotectant to between −10° C. to −40° C., cutting the frozen tissue matrix, placing the cut tissue matrix in a liquid to form a suspension, and freeze-drying the suspension. In addition, in various embodiments, tissue matrices produced according to the methods described herein are provided. In certain embodiments, a tissue matrix composition is provided. The composition comprises a collagen-based tissue matrix, wherein the matrix has been contacted with a cryoprotectant solution and frozen thereafter, and wherein the matrix has been cut after freezing at a temperature between −10° C. and −40° C. In certain embodiments, an additional tissue matrix composition is provided. The composition comprises a collagen-based tissue matrix, wherein the tissue matrix comprises particles having a size distribution ranging from 0.2-5 mm in length, 0.2-3 mm in width, and 0.02-0.3 mm in thickness.

After a tissue matrix has been selected, a cryoprotectant solution is used to treat the tissue matrix prior to freezing. The cryoprotectant solution prevent damage to the tissue from damage as a result of freezing and/or thawing, reduce the amount of frozen water in the tissue through osmotic dehydration, and can ensure the formation of a high subzero temperature glassy matrix in the tissue. The use of a cryoprotectant can also help maintain a desired balance between ice content and non-frozen tissue after freezing. A frozen tissue matrix containing too much ice can be brittle and difficult to cut. Conversely, frozen tissue matrix with insufficient ice is too soft and warms rapidly during cutting, making it difficult to cut as well. Thus, the concentration of the cryoprotectant in the cryoprotectant solution can be used to control the ice content and hardness of the frozen matrix.

In some embodiments, the ice content of the frozen matrix (w/w) ranges from 40-60% (e.g., 40, 45, 50, 55, or 60%).

Any suitable cryoprotectant can be used in the cryoprotectant solution. In certain embodiments, suitable cryoprotectants can include maltodextrin, sucrose, polyethylene glycol (PEG), and polyvinylpyrrolidone (PVP), or combinations thereof. In some embodiments, the cryoprotectant comprises maltodextrin. In some embodiments, the cryoprotectant solution contains 5-50% (w/v) maltodextrin. In some embodiments, the solution contains 15-25% (w/v) maltodextrin.

After treatment with the cryoprotectant solution, the tissue matrix is then frozen. In certain embodiments, the tissue matrix is frozen at −80° C. Freezing can be accomplished by using a −80° C. freezer. Before cutting, the temperature of the tissue matrix can be adjusted if needed to a temperature ranging from −10° C. to −40° C. for the cutting step. That temperature range can help maintain the proper balance between ice content and non-frozen tissue, which facilitates cutting.

After adjusting the temperature, the tissue can be cut. In some embodiments, the tissue is cut into pieces of irregular shape and size. In some embodiments, the irregular shape and size gives the cut tissue a flake-like appearance. In other words, the pieces of cut tissue encompass irregular shapes and sizes, and lack consistency between pieces. In some embodiments, the cut tissue has a selected size distribution. In certain embodiments, the cut tissue has a size distribution ranging from 0.2-5 mm in length, 0.2-3 mm in width, and 0.2-0.3 mm in thickness. When hydrated, the majority of cut tissue within this size distribution weighs between 0.5 and 2.0 mg. The irregular shape and size distribution of the cut tissue facilitate the formation of large, interconnected channels that permit body fluid to flow freely when the cut tissue is placed in suspension, and thus aid host cell repopulation and revascularization. In some uses, the large size of the cut tissue, relative to smaller micronized tissue particles, prevents migration of the cut tissues into surrounding anatomic sites when implanted or placed in or on a wound. Cut tissue that is larger than the disclosed size distribution may also be undesirable. If the cut tissue is too large, the individual pieces may take up too much space when in suspension and also impede formation of sufficiently large channels.

Various methods can be used to cut the tissue and still be in accordance with the disclosed method, provided the tissue is cut into pieces of irregular shape and size. For example, the tissue matrix can be cut manually, using scissors. In some embodiments, cutting the tissue matrix comprises grating the tissue matrix. In some embodiments, a grating device is used to perform the grating step. Any grating device can be used in accordance with the disclosed method, provided it cuts the tissue matrix into pieces of irregular size and shape. In some embodiments, the grating device is a grater, such as a MICROPLANE® grater. In other embodiments, the grating device is a grating wheel.

In certain embodiments, the cutting step can be automated. Automating reduces the amount of time necessary to prepare the cut tissue and facilitates cutting larger amounts of tissue. In various embodiments, one or more aspects of the cutting process can be automated. For example, the grating device itself can be automated so that manual effort is no longer required to cut the tissue matrix. It is also possible to automate delivery of the tissue matrix to the cutting device. Further, it is possible to automate removal of tissue matrix once it has been cut. One example of an automated cutting apparatus is illustrated in FIG. 1. As shown, the apparatus comprises a grating wheel 101 that is fitted with blades 102 for cutting a matrix 107. Below the grating wheel is a collection tray 103. The grating wheel 101 and collection tray are enclosed in a housing unit 104, which protects the operator from direct contact with the blades 102. The housing unit 104 is fitted with a loading bay 106. In this example, the loading bay 106 is inclined so that any samples loaded onto it will move toward the grating wheel 101 by gravity. Tissue matrix 107 is placed onto the loading bay 106 and moves toward the grating wheel 101. The blades 102 of the grating wheel 101 cut the tissue matrix 107 into flakes 108 which fall into the collection tray 103 below.

In various embodiments, the disclosed methods can further comprise additional processing before or after cutting. For example, in various embodiments, the disclosed methods comprise use of a pre-processed acellular tissue matrix, which is described in more detail below. In other embodiments, an intact, cellular tissue may be used, which can be further processed to produce a suitable acellular tissue matrix. The further processing may comprise decellularization, DNA removal, and removal of α-gal epitopes or other antigens. Decellularization, DNA removal, and α-gal antigen removal are described in further detail below. Further processing of the cut tissue may include disinfecting the tissue matrix. In some embodiments, the flake-like tissue matrix is disinfected with isopropyl alcohol (IPA) (e.g., at about 70% IPA).

Processing of the tissue flakes is also amenable to automation. Automation can include any process that does not require the manual delivery and removal of the solutions that facilitate processing. Automation of tissue processing reduces time spent manually replacing processing solutions and minimizes operator handling of the tissue flakes. In some embodiments, automation of tissue processing comprises use of a closed, low-pressure perfusion column. Decellularization, DNA removal, α-gal antigen removal, and disinfection can all be performed within the column, which allows for high-throughput processing of the cut tissue. Cut tissue matrix is loaded into the column, and air is purged from the column. Decellularization, DNA removal, α-gal antigen removal, and disinfection are achieved by stepwise perfusion of the appropriate solutions at or near atmospheric pressure. Detergent, DNAse, and α-galactosidase solutions are described in more detail below.

Figure 2:
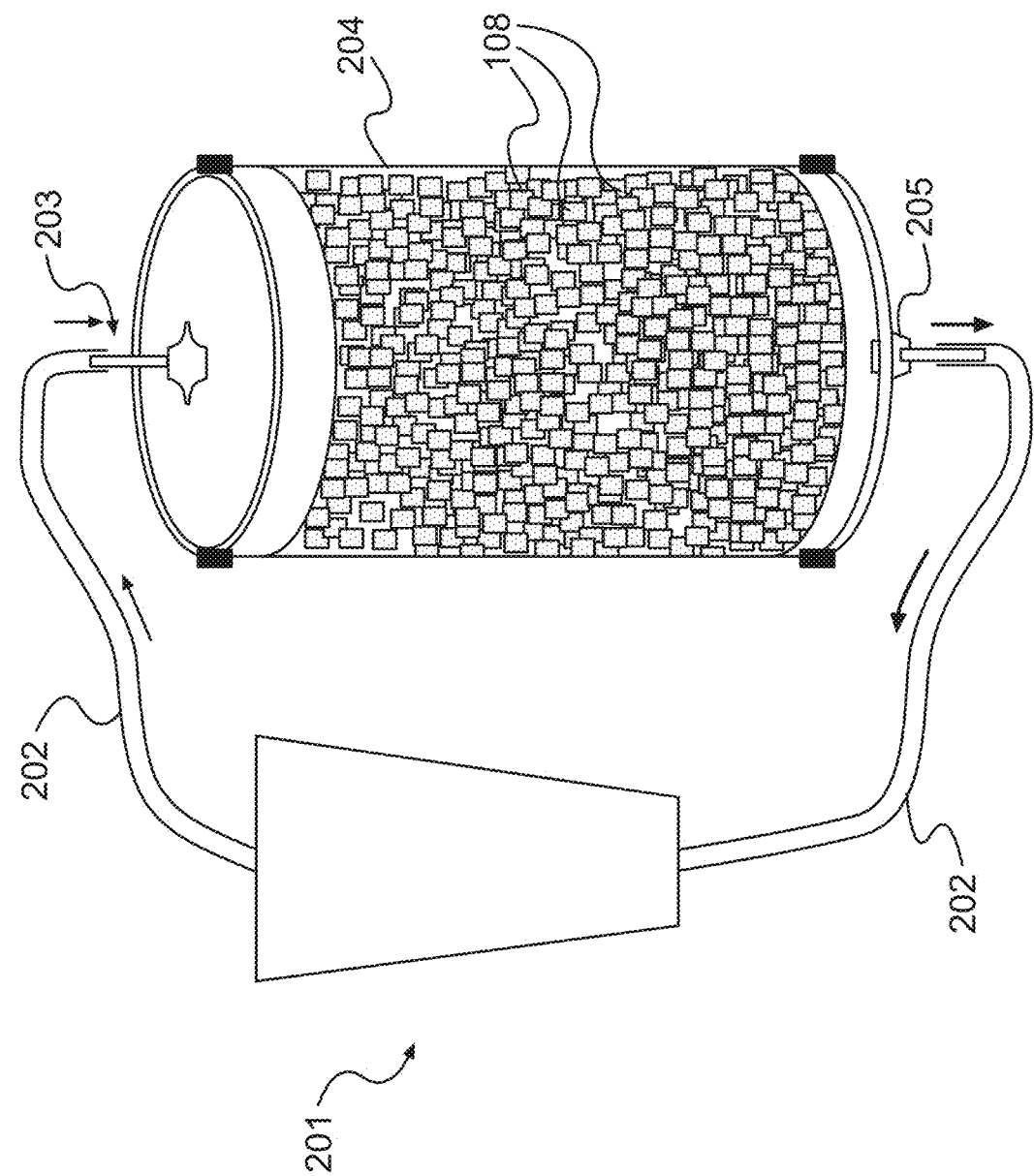
FIG. 2 is a diagram of a perfusion column for producing tissue fillers of the present disclosure, according to certain embodiments.

An example of an automated processing system is shown in FIG. 2. The processing system comprises a solution pumping into which various processing solutions are placed. The pumping system 201 sends an appropriate solution through tubing 202 into a closed perfusion column 204, which has been fitted with a process solution inlet 203 and outlet 205. The appropriate solution then contacts the tissue flakes 108 inside the perfusion column 204 and then leaves the column 204 through tubing 202 connected to the process solution outlet 205 on one end and the solution pumping system 201 on the other end.

The disclosed tissue fillers can be further treated to produce substantially aseptic or sterile materials. Accordingly, in various embodiments, the tissue fillers can be sterilized after preparation. As used herein, a "sterilization process" can include any process that reduces bioburden in a sample, but need not render the sample absolutely sterile.

Certain exemplary processes include, but are not limited to, a gamma irradiation process, an e-beam irradiation process, ethylene oxide treatment, and propylene oxide treatment. Suitable sterilization processes include, but are not limited to, those described in, for example, U.S. Patent Publication No. 2006/0073592A1, to Sun et al.; U.S. Pat. No. 5,460,962 to Kemp; U.S. Patent Publication No. 2008/0171092A1, to Cook et al. In some embodiments, sterilization is performed in conjunction with packaging of the flakes, while in other embodiments, sterilization can occur after packaging.

After the tissue flakes are prepared by the disclosed methods, they may be stored for some time before implantation in or on a patient. In certain embodiments, the tissue filler may be packaged in a Tyvek pouch for storage purposes. The tissue filler may also be stored in different states. In some embodiments, the flake-like tissue filler is freeze-dried after preparation. In certain embodiments, freeze-drying of the flake-like tissue filler is performed before or during packaging. In certain embodiments, the tissue flakes are stored in a hydrated state. The tissue flakes can be hydrated in various solutions, for example, an aqueous preservation solution.

The various steps described above can be combined, added, deleted, or otherwise modified as necessary. For example, if the starting material is a porcine hide, removing the epidermis and subcutaneous fat may be necessary before cutting. However, removal of those components is not required if the starting material is an acellular tissue matrix. Further, if one is using porcine hide as the starting material rather than an acellular tissue matrix, additional processing may be necessary after cutting.

Figure 3:
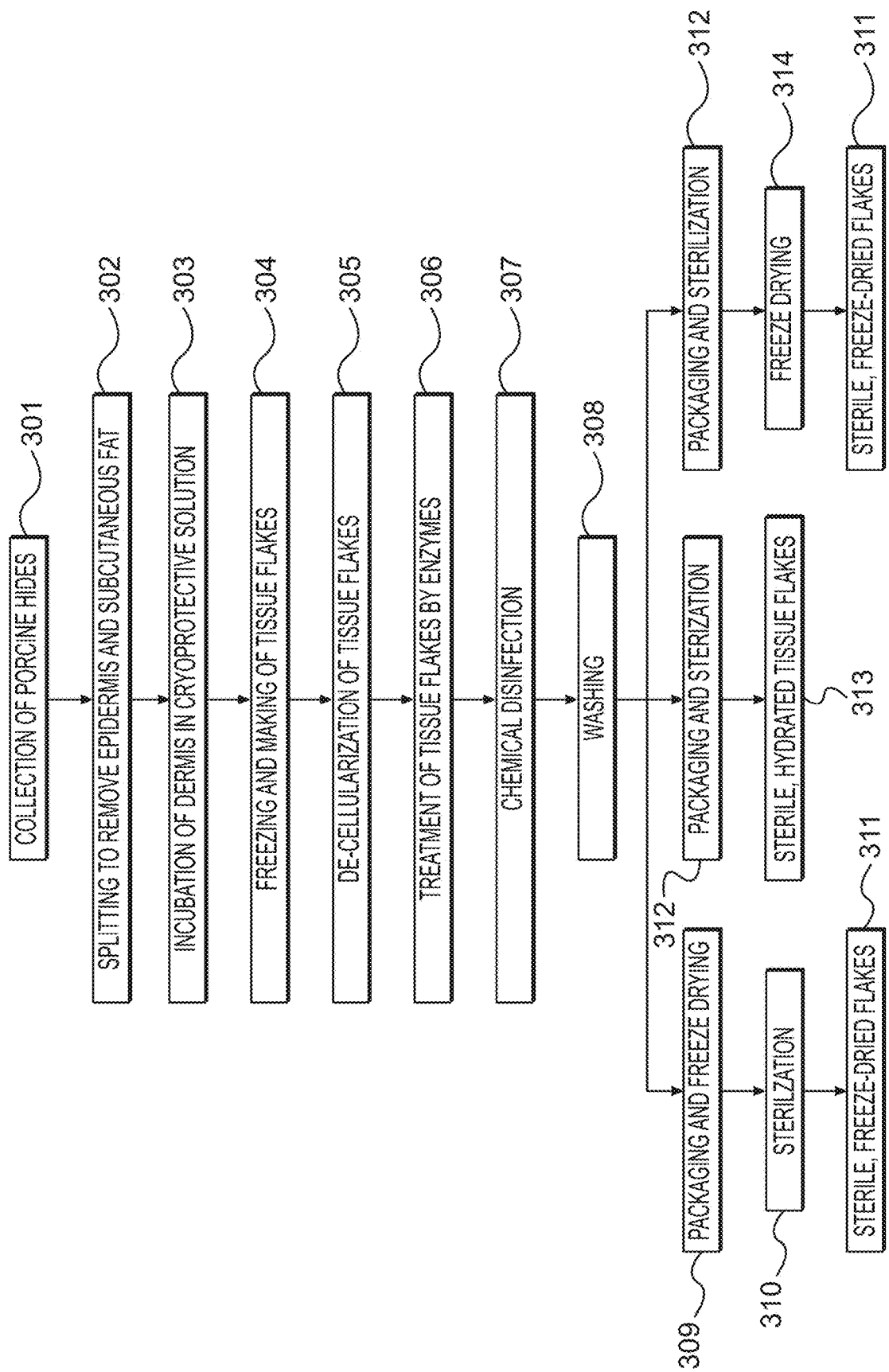
FIG. 3 is a flow chart summarizing the various steps that may be used to produce tissue fillers, according to certain embodiments of the disclosed method.

A sample protocol in accordance with the disclosed methods is provided in FIG. 3, using porcine hides as the starting material. Specific details regarding each step are provided throughout the present disclosure. Fresh porcine hides are collected with the hairs subsequently removed 301. The epidermis and subcutaneous fat layers are then removed, leaving the dermal tissue 302. The dermal tissue is then incubated in a cryoprotectant solution prior to freezing to maintain the proper balance between ice content and amorphous tissue during cutting 303. After incubation in the cryoprotectant solution, the tissue is frozen, brought to a temperature between $-10°$ C. and $-40°$ C., and cut to a desired size and shape. The flakes are then incubated in an appropriate solution to decellularize the tissue 305. The tissue is then treated with treated with enzymes to remove DNA and α-gal epitopes 306. After enzyme treatment, the flakes are disinfected with using an IPA solution 307 and washed in buffer 308.

After washing, the tissue flakes are packaged for storage. Packaging can be performed in conjunction with freeze-drying 309 or with sterilization 312. If the flakes are freeze-dried in conjunction with packaging 309, they are then sterilized 310, resulting in sterile, freeze-dried flakes 311. Alternatively, if packaging and sterilization are performed together 312, the flakes can be freeze-dried after 314, which also results in sterile, freeze dried flakes 311. The flakes can also be hydrated after the packaging and sterilization step 312, resulting in sterile, hydrated tissue flakes 313.

The disclosed tissue matrix composition can be used in various ways. In certain embodiments, the tissue matrix composition can form a stable, non-gelling, low density suspension. In certain embodiments, the disclosed tissue matrix composition can be used as a bulk tissue filler for tissue regeneration and repair. Methods of treatment using the composition include selecting an anatomical site for treatment and implanting the tissue filler into the treatment site. Examples include the direct application of the flake-like tissue material to deep wounds and large soft tissue voids that may occur during certain types of surgeries, such as lumpectomies. The tissue filler may be also be used in the treatment of pressure ulcers, diabetic foot ulcers, or periosteal bone defects. The tissue filler can also be used for reconstructing facial features as well as correcting facial defects, including treatment of wrinkles, skin loss, or skin atrophy. In other embodiments, the flake-like tissue material may be used as a carrier for controlled delivery of other bioactive substances. Examples of bioactive substances include, but are not limited to, antimicrobial agents, cytokines, growth factors, and drugs. Bioactive substances can also include non-collagenous tissue, such as adipose tissue, or cells, including stem cells. In certain embodiments, tissue flakes that have been subsequently freeze-dried can be hydrated in solutions that contain bioactive substances, and then applied to the sites as needed. In other embodiments, the flake-like tissue filler can be applied as a slurry. If an aqueous suspension of tissue flakes is blended briefly (30 to 300 seconds, for example), it becomes a loosely intertwined fibrillar slurry that is flowable for convenient application.

In certain instances, a tissue foam may be desired. Depending on the surgical procedures and particular circumstances of tissue repair, use of a tissue foam may be appropriate. Tissue foams can be used to treat wounds or damaged tissues that are not defined by voids with a particular boundary. For example, one could use surgical adhesives or sutures to attach a tissue foam to tissues or organs. In other cases, tissue flakes may be more desirable when there is a need to fill voids of any shape, which are defined by a particular boundary. For example, tissue flakes are suitable when tumors are removed via laproscopic procedures or cryosurgery, due to the small openings that result. Tissue foams can also be made to have specific sizes and shapes, such as sheets, spheres, and cubes, for certain well-defined surgeries. For example, tissue foam sheets can be used to partially or completely cover surgical implants to reduce the dramatic effect of initial implant/body interactions and potentially slow capsule formation. Further, tissue foams can be used as components of negative pressure wound therapy systems, such as the VAC® system, which is produced by Kinetic Concepts, Inc. Such systems can be used to treat a variety of tissues sites and include, for example, a negative pressure source such as a pump and one or more treatment materials, which often include a porous foam or manifold. General examples of such systems are described in U.S. Patent Publication Number, 2010/0040687 A1, which was filed on Aug. 13, 2009.

The use of the disclosed tissue flakes facilitates the preparation of tissue foam in several ways. The tissue flakes have a small mass but large surface area, which facilitates further processing, and the flakes are amenable to preparing a uniform fiber suspension. In contrast to using ground or micronized tissue particles or fibers, tissue flakes are unlikely to gel or cake during decellularization. Finally, the process of preparing the tissue flakes first adds an additional layer of size reduction, which assists in the preparation of a uniform suspension.

Accordingly, the methods described herein can also be used to prepare a regenerative foam using the cut tissue described above as the starting material. As discussed above, a tissue matrix is selected and a cryoprotectant is used to treat the tissue matrix prior to freezing. The tissue matrix is then frozen and cut at a temperature ranging from −10° C. to −40° C. after freezing. As before, a pre-processed, acellular tissue matrix may be used in conjunction with the disclosed method. In other embodiments, the tissue matrix can be decellularized after cutting as described above.

The cut tissue matrix is then placed in a liquid to form a suspension. Any suitable liquid may be used, provided it does not interfere with the regenerative properties of the tissue matrix. In some embodiments, the cut tissue matrix is placed in an aqueous solution. After being placed in solution, the tissue matrix can be mixed within the solution. In various embodiments, the solution is mixed until a stable tissue suspension is formed, and/or until the tissue size distribution reaches a desired level. Mixing can be accomplished by any suitable means that achieve these ends, such as agitating, shaking, or vortexing the tissue matrix once it is in solution. Blending can also be used to mix the tissue matrix in solution. In certain embodiments, a blender is used to mix the matrix. Mixing may also be achieved by using a pressure jet, an ultrasound device, or a combination of the two. For example, after decellularization, tissue flakes in solution can go through a pressurized nozzle, where the tissue flakes break into fibers. One can also place tissue flakes in solution into an ultrasonic field to break the tissue flakes into a fiber suspension. A sonic nozzle can also be used, which combines ultrasound and pressure to break the tissue flakes into a fibrous suspension. The consistency of the suspension can be controlled by how much cut tissue matrix is added to the liquid. In some embodiments, the amount of cut tissue matrix in the liquid ranges from 20-40% (w/v). In certain embodiments, the amount of cut tissue matrix in the liquid is 25% (w/v).

After formation of a suspension, the tissue suspension is then freeze-dried. Freeze-drying can be performed under aseptic conditions to prevent contamination of the tissue matrix. The tissue suspension can also be aliquoted into an appropriate container, so that upon freeze-drying, the tissue matrix will be cast in the desired shape.

The process of mixing and freeze-drying results in a tissue composition wherein small tissue filaments of various dimensions are intertwined and interlocked with one another. In certain embodiments, the process of mixing and freeze-drying the tissue suspension results in a tissue foam. A foam can be produced, for example, by blending an aqueous suspension freeze-dried tissue flakes in a blender. After processing, the tissue composition contains interconnected macropores due to the intertwined pieces of small tissue, which permit the free flow of fluid and help support cell repopulation and revascularization.

The tissue foam disclosed herein can be further processed as needed. The tissue foam can be disinfected or sterilized as described above. The freeze-dried material can also be further treated to increase the strength of the tissue foam using heat and vacuum conditions. Without being bound to theory, strengthening of the tissue foam may occur through physical interlocking, biochemical cross-linking, or a combination of the two. Physically, final dehydration results in surface tension, which pulls tissue fragments closer together and forms hydrogen bonds between the hydroxyl groups of adjacent collagen fibers. Chemically, the treatment results in amide formation between carboxyl and amino groups, as well as esterification and glycation of collagen and other extracellular matrix protein amino groups. In some embodiments, the heat applied to the tissue matrix is limited to avoid denaturation of the dry proteins contained in the tissue matrix. Dry proteins in the tissue matrix typically denature between 130° C. and 170° C. In one embodiment, the strength of the tissue foam can be increased by treating the freeze-dried material at a temperature above 30° C. but below the denaturation temperatures listed above under vacuum conditions. In some embodiments, the strength of the tissue foam can be increased by treating the freeze-dried material at approximately 100° C. under vacuum for a certain period of time. In some embodiments, the dried material may be treated under for vacuum for 24 hours. Other suitable periods of time can be readily identified and tested by those skilled in the art.

After processing, the tissue foam may be stored for some time before implantation in or on a patient. In certain embodiments, the tissue foam may be packaged in a Tyvek pouch for storage purposes. The tissue foam itself may also be stored in different states. In some embodiments, the tissue foam is stored in its already freeze-dried state. In other embodiments, the tissue foam is stored in a hydrated state.

Tissue Matrices

As noted above, the methods described herein can be used to produce flake-like tissue fillers using a variety of different tissue types, so long as the tissue includes a collagen-containing matrix amenable for use with the methods described above. Such tissue matrices can include intact tissues, tissues that have been partially or completely decellularized, or synthetic collagenous matrices (e.g., 3-D matrices formed from suspended or otherwise processed tissues).

The tissue matrix can be produced from a range of tissue types. For example, the tissue matrix can be derived from fascia, pericardial tissue, dura, umbilical tissue, placental tissue, cardiac valve tissue, ligament tissue, tendon tissue, arterial tissue, venous tissue, neural connective tissue, urinary bladder tissue, ureter tissue, and intestinal tissue. In other embodiments, the tissue matrix comprises a dermal tissue matrix. In certain embodiments, the tissue matrix comprises porcine dermal matrix.

In certain embodiments, the tissues can include a mammalian soft tissue. For example, in certain embodiments, the tissue can include mammalian dermis. In certain embodiments, the dermis can be separated from surrounding epidermis and/or other tissues, such as subcutaneous fat. In certain embodiments, the tissue sample can include small intestine submucosa. In certain embodiments, the tissue samples can include human or non-human sources. Exemplary, suitable non-human tissue sources include, but are not limited to, pigs, sheep, goats, rabbits, monkeys, and/or other non-human mammals.

The tissue matrices can be implanted at a variety of different anatomic sites. For example, tissue matrices can be implanted around breast implants; around or replacing vascular structures; around or replacing luminal structures (e.g., ureters, nerves, lymphatic tissues, gastrointestinal structures); on or replacing heart valves, pericardium, or other cardiac structures; in or on bony or cartilaginous materials (e.g., ears, noses, articular surfaces, around dental structures, or along any short of long bone); and/or surrounding, lining, supporting, or replacing any body cavity (e.g., bladder, stomach).

Tissue matrices can be selected to provide a variety of different biological and mechanical properties. For example, an acellular tissue matrix can be selected to allow tissue ingrowth and remodeling to assist in regeneration of tissue normally found at the site where the matrix is implanted. For example, an acellular tissue matrix, when implanted on or into fascia, may be selected to allow regeneration of the fascia without excessive fibrosis or scar formation. In certain embodiments, the tissue matrix can be formed from ALLODERM® or STRATTICE™, which are human and porcine acellular dermal matrices, respectively. Alternatively, other suitable acellular tissue matrices can be used, as described further below.

In some embodiments, the collagen-based material comprises an acellular tissue matrix. In certain embodiments, these matrices can be completely decellularized to yield acellular tissue matrices to be used for patients. For example, various tissues, such as skin, intestine, bone, cartilage, nerve tissue (e.g., nerve fibers or dura), tendons, ligaments, or other tissues can be completely decellularized to produce tissue matrices useful for patients. Suitable processes for producing acellular tissue matrices are described below.

In general, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. For example, in some embodiments, 2% sodium deoxycholate is added to the decellularization solution.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable buffer can be used as long as the buffer provides suitable DNase activity.

While an acellular tissue matrix may be made from the same species as the acellular tissue matrix graft recipient, different species can also serve as tissue sources. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., *J. Biol. Chem.* 263:17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., *Infect. Immun.* 56:1730 (1988); R. M. Hamadeh et al., *J. Clin. Invest.* 89:1223 (1992).

Since non-primate mammals (e.g., pigs) produce α-gal epitopes, xenotransplantation of collagen-containing material from these mammals into primates often results in immunological activation because of primate anti-Gal antibodies binding to these epitopes on the collagen-containing material. U. Galili et al., *Immunology Today* 14:480 (1993); M. Sandrin et al., *Proc. Natl. Acad. Sci. USA* 90:11391 (1993); H. Good et al., *Transplant. Proc.* 24:559 (1992); B. H. Collins et al., *J. Immunol.* 154:5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896, 594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," *Tissue Engineering*, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

Although general process parameters for production of acellular tissue matrices are described, a variety of collagen-containing acellular materials are available, and the methods of processing such materials to produce flake-like tissue fillers may be used with any of those materials. For example, a number of biological scaffold materials are described by Badylak et al., and the methods of the present disclosure can be used to produce flake-like tissue fillers using any of those materials, or any other similar materials. Badylak et al., "Extracellular Matrix as a Biological Scaffold Material: Structure and Function," *Acta Biomaterialia* (2008), doi: 10.1016/j.actbio.2008.09.013.

Example 1

Cryopreservation and Cryocutting of Split Porcine Dermis

Fresh porcine hides were collected, and the hair was removed. Dermis tissue was obtained from the hides by splitting off the epidermis layer and subcutaneous fat (hypodermis) layer. The porcine dermis was rinsed with Dulbecco's phosphate-buffered saline (PBS), and incubated for 4 to 6 hours in a cryoprotectant solution containing 50 mM sodium phosphate, 10 mM ethylenediamine tetraacetic acid (EDTA) and 35% (w/v) maltodextrin (pH 7.0). Cryoprotectant-treated dermis sheets were then frozen in a −80° C. freezer. Frozen dermis tissue was grated into tissue flakes by using a medium-sized MICROPLANE® grater (grater openings are approximately 2.2 to 3.2 mm wide and 0.2 mm thick).

Figure 4B:
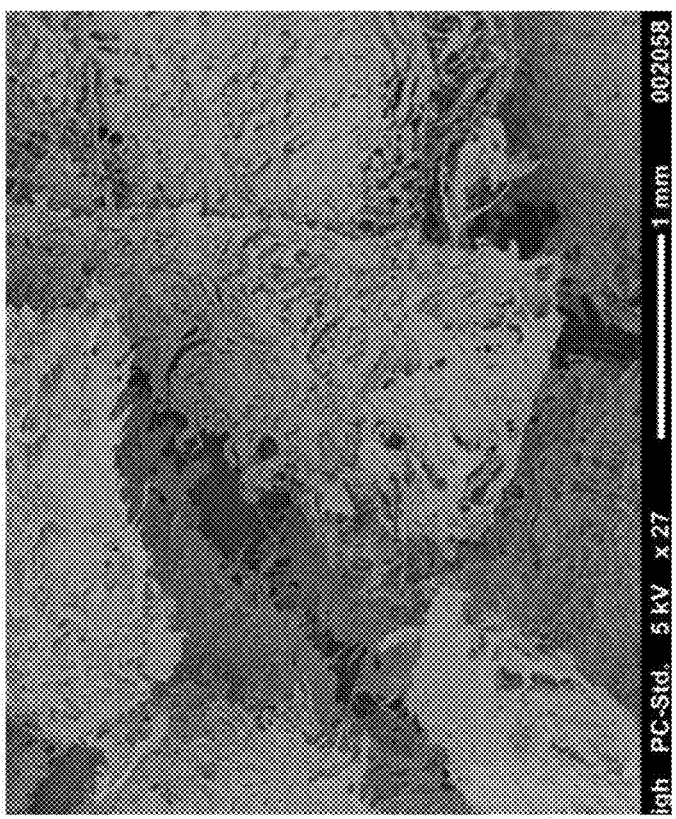
FIGS. 4A and 4B are photographs demonstrating the morphology of various tissue pieces under light and SEM microscopy respectively, according to certain embodiments, as described in Example 1.
Figure 4A:
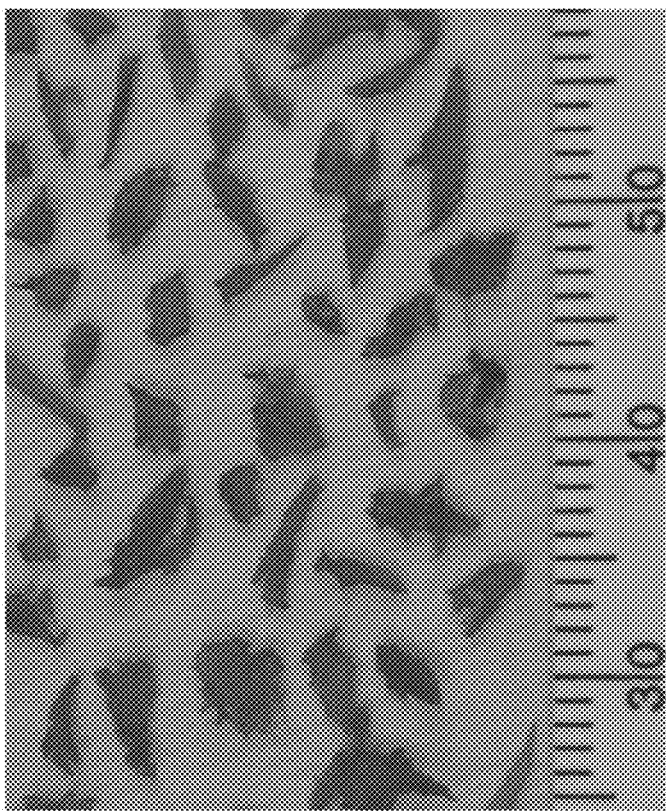

The tissue flakes were then washed for 10-15 minutes in PBS to remove the cryoprotectant and then fixed in 2% glutaraldehyde solution. The morphology of the tissue flakes was then observed using light microscopy and scanning electron microscopy (SEM). For examination under light microcopy, tissue samples were stained with Sirius Red. For SEM examination, tissue samples were dehydrated stepwise in ethanol solutions of increasing concentration (25%, 50%, 75%, 90%, 95%, 98% and 100%), dried with supercritical $CO_2$ in a critical point dryer, and sputter-coated with gold. Tissue specimens were viewed under high vacuum and low electron voltage (5 kV). As shown in FIGS. 4A and 4B, the morphology of the cut pieces was observed to be flake-like under both types of microscopy.

Figure 5:
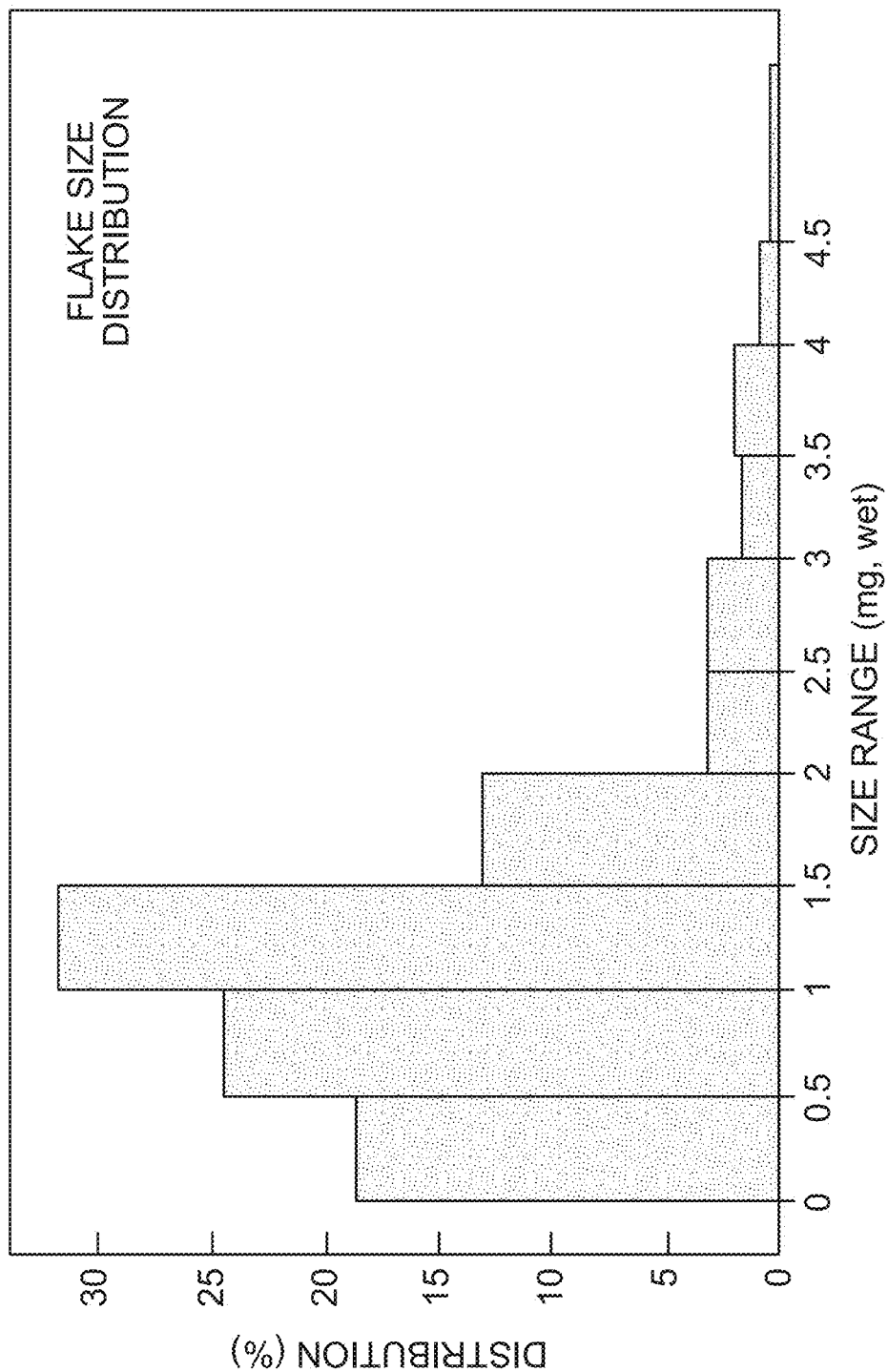
FIG. 5 is a chart showing the distribution of tissue flake size according to certain embodiments, as described in Example 1.

To determine the size (mass) distribution of the tissue flakes, glutaraldehyde-fixed tissue pieces were washed in distilled water to remove glutaraldehyde residue. The wet weight of greater than 200 tissue pieces was determined after blot-drying surface water with surgical gauze. FIG. 5 shows the mass-based size distribution of the tissue flakes. More than 70% of the tissue fragments weighed between 0.5 and 2.0 mg, with an average weight of 1.3 mg. Few tissue pieces weighed over 4 mg. The tissue fragment size was in the expected range after using a medium microplane (2 to 3 mm wide and 0.2 mm thick, nominal tissue volume of 0.8 to 1.8 mm$^3$).

Example 2

Control of Ice Content in Frozen Porcine Dermis

The proper ratio between ice and amorphous phase frozen dermis tissue facilitates cutting dermis sheets into a flake-like tissue matrix. Frozen dermis sheets that were not treated in cryoprotectant solution contained too much ice, were too brittle, and were difficult to cut. On the other hand, frozen dermis sheets with low ice content were soft and warmed rapidly during cutting, also making them difficult to cut. The ice content and the hardness of the frozen dermis sheets were controlled by pretreating the dermis sheets in cryoprotectant solutions that reduced ice formation while facilitating formation of an amorphous tissue matrix with a high subzero glass transition temperature.

Figure 6:
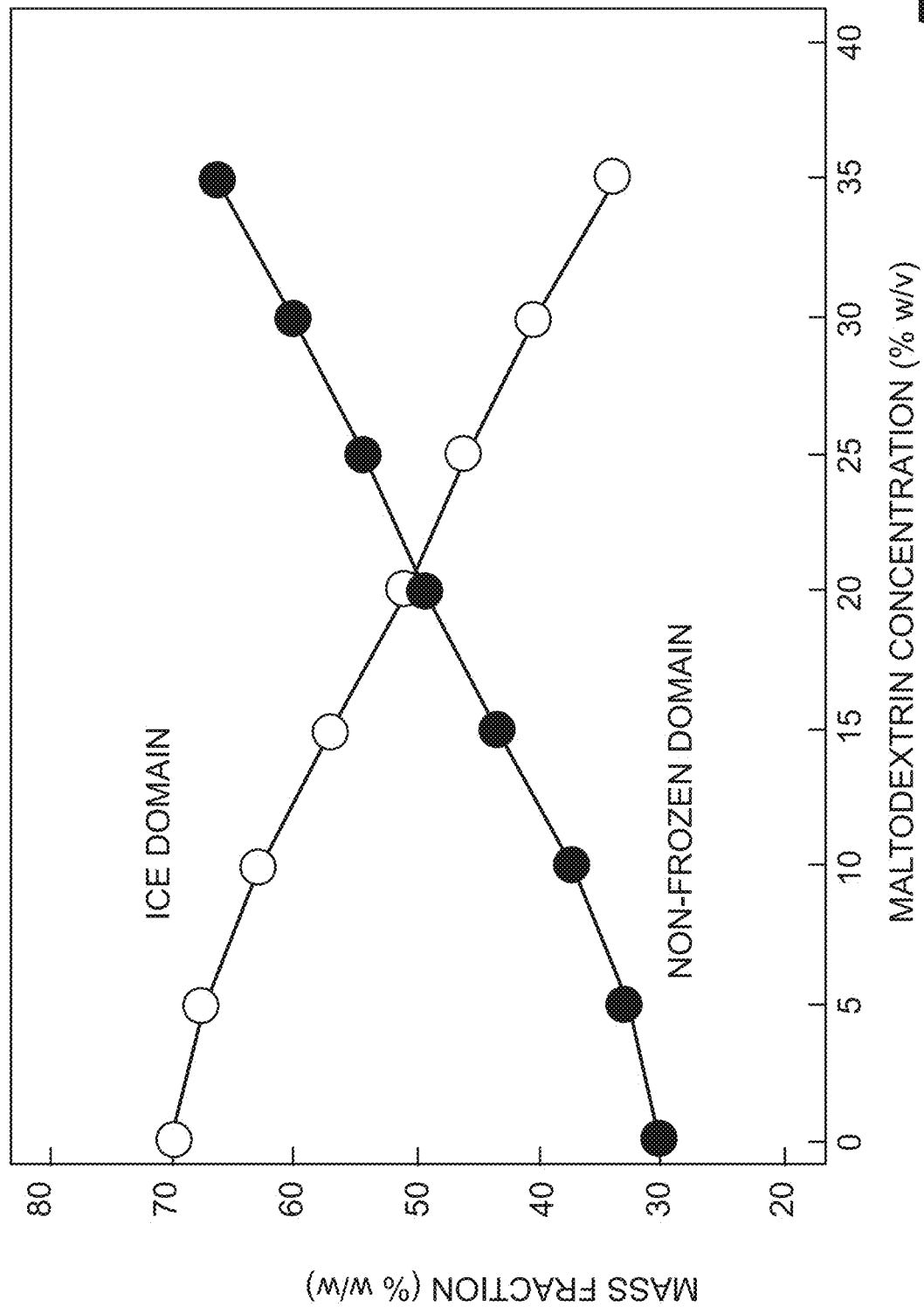
FIG. 6 is a chart showing the mass fractions of ice and amorphous tissue domain as a function of cryoprotectant concentration, according to certain embodiments, as described in Example 2.

Split porcine dermis was prepared as described in Example 1. Maltodextrin solutions containing 0% to 35% (w/v) maltodextrin were made with phosphate buffer solution (50 mM sodium phosphate, 10 mM EDTA, pH 7.0). Samples of split porcine dermis were incubated in the cryoprotectant solutions overnight. After incubation, water and cyroprotectant content in dermis tissue samples were determined. Ice contents of frozen tissue samples were determined by differential scanning calorimetry according to their ice melting enthalpies. FIG. 6 shows the mass fractions of ice and amorphous tissue domain in the frozen tissue pretreated in different cryoprotectant solutions. In the absence of maltodextrin (PBS buffer alone), porcine dermis had 75% (w/v) water and 25% dry mass. Upon freezing, ~93% of dermis water crystallized as ice, resulting in a mass fraction of 70% ice and a mass fraction of 30% freeze-concentrated amorphous (non-frozen) domain. The corresponding volume fractions were 77% and 23% for ice and non-frozen domain, respectively. With increasing maltodextrin concentrations, the ice fraction of incubated porcine dermis tissue decreased and the fraction of the non-frozen domain increased. For porcine dermis incubated in 35% maltodextrin solution, the mass fractions of ice and non-frozen domain were reduced to 34% and increased to 66%, respectively (corresponding volume fractions of 42% and 58%, respectively). Reduced ice formation was due to both osmotic tissue dehydration and maltodextrin penetration into the extracellular matrix of the dermis tissue. As a result of maltodextrin penetration into the dermis extracellular matrix, the glass transition temperature of the frozen dermis amorphous domain increased to −17° C. Porcine tissue treated with 15-35% maltodextrin solutions could be easily grated into tissue flakes.

Example 3

Processing of Dermal Tissue Flakes

Tissue flakes prepared as described in Example 1 were further processed to remove cellular components and α-galactosyl epitopes. The process included the following steps: (i) rinsing off the cryoprotectants, (ii) decellularization, (iii) enzyme treatment, (iv) disinfection, (v) freeze drying, (vi) sterilization, and (vii) secondary packaging.

(i) Removal of cryoprotectants. Tissue flakes were placed into 225 mL conical centrifuge bottles (~30 g/bottle). The material was washed with 150 mL of sterile PBS for about 10 minutes. The tissue suspension was centrifuged at 500 rpm for 3 minutes, and the supernatant was discarded. The tissue pellet was re-suspended with 150 mL sterile distilled water, and centrifuged again at 500 rpm for 3 minutes to collect the tissue flakes.

(ii) Decellularization. Tissue material was decellularized at ambient temperature with agitation in 150 ml of 2% (w/v) sodium deoxycholate dissolved in 10 mM HEPES buffer with 10 mM EDTA (pH 7.8). Decellularization solution was changed after 1 hour through centrifugation at 500 rpm for 3 minutes. After fresh solution was added, the tissue material was allowed to incubate for another 4 hours. Decellularization solution was drained after another round of centrifugation.

(iii) Enzyme treatment. Decellularized tissue flakes were washed twice for 30 minutes at a time with 10 mM HEPES buffer containing 5 mM EDTA (pH 7.3). Enzyme treatment was carried out for 4 hours in 150 mL of HEPES buffer with 2 mM $MgCl_2$, 2 mM $CaCl_2$, 1 mg/L dornase alfa, and 1 mg/L α-galactosidase. Enzyme solution was drained after centrifugation at 500 rpm for 3 minutes.

(iv) Disinfection. Enzyme-treated tissue flakes were re-suspended and washed twice with 10 mM HEPES buffer with 5 mM EDTA. The first wash was for 60 minutes and the second wash was conducted overnight. After centrifugation, the tissue material was rinsed with 100 mL sterile distilled water for 30 minutes. For some bottles, 100 mL isopropyl alcohol (IPA) solution (70% w/v) was added to the tissue suspension. After about 10 minutes, the suspension was centrifuged at 500 rpm for 3 minutes. Old IPA solution was drained, and fresh 70% IPA solution was added to re-suspend the material. The material was treated with IPA for at least 4 to 6 hours before being packaged in Tyvek bags for freeze drying. For other bottles, tissue flakes were directly packaged in Tyvek bags for freeze-drying without IPA disinfection.

(v) Freeze drying. Processed tissue material was freeze-dried. Freeze-drying consisted of 3 stages: (a) cooling the material from room temperature to −35° C. at ~1° C./minute, then holding at −35° C. for 10 minutes; (b) ramping up to −10° C. at ~1° C./minute under 40 mT, then holding for 16 hours; and (c) ramping up to 20° C. at ~1° C./minute under 20 mT and then holding for 8 hours.

(vi) Sterilization. Freeze-dried tissue samples that were not disinfected with IPA were sterilized with ethylene oxide (EO). EO sterilization included (a) conditioning at 52° C. to 63° C. and 55 to 75% Relative Humidity for 30 to 45 minutes, (b) EO exposure with a gas concentration of 600±50 mg/L for 4 hours, and (c) aeration at 38 to 54° C. for at least 12 hours.

(vii) Secondary packaging. IPA-treated samples were packaged immediately into foil-to-foil bags after freeze-drying. EO treated samples were packaged in foil-to-foil bags following EO treatment.

The processed tissue flakes were acellular. Both IPA-treated and EO-treated materials tested to be sterile.

Example 4

Stability of Processed Tissue Flakes

Figure 7:
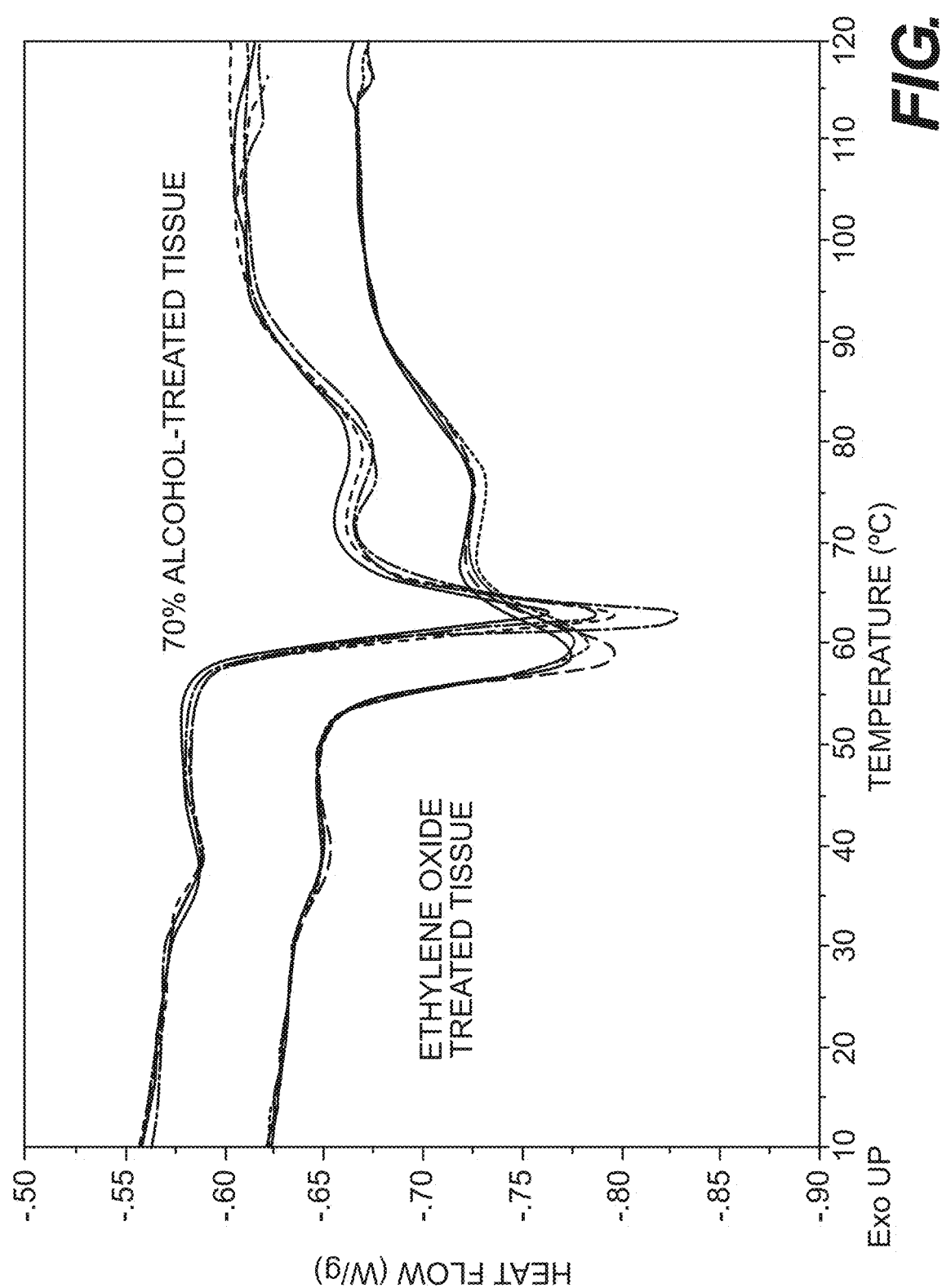
FIG. 7 is a chart showing thermograms of tissue flakes according to certain embodiments, as described in Example 4.

Thermal stability of processed tissue flakes was tested using differential scanning calorimetry (DSC). Both IPA-treated and EO-treated materials were rehydrated in PBS saline (pH 7.5). Samples were scanned at a heating rate of 3° C./min from 2 to 125° C. (DSC Q200, TA Instruments). Both IPA-treated and EO-treated tissue had a small low temperature peak (~30 to 32° C.). As shown in FIG. 7, the onset temperature of the major collagen denaturation peaks was 53.3±0.2° C. and 58.0±0.2° C. (N=4) for EO-treated tissue flakes and IPA-treated tissue flakes, respectively. The onset temperature of IPA-treated tissue flakes was similar to the fresh dermis samples. The data indicated that EO sterilization destabilizes tissue matrix compared to IPA treatment.

Figure 8B:
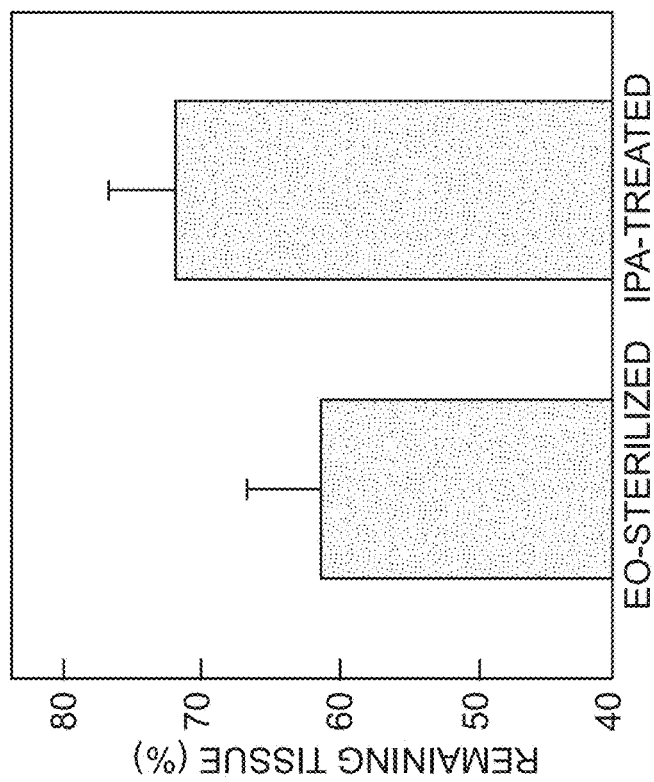
FIGS. 8A and 8B are charts showing the resistance of processed tissue material, according to certain embodiments, to collagenase and trypsin digestion, respectively, as described in Example 4.
Figure 8A:
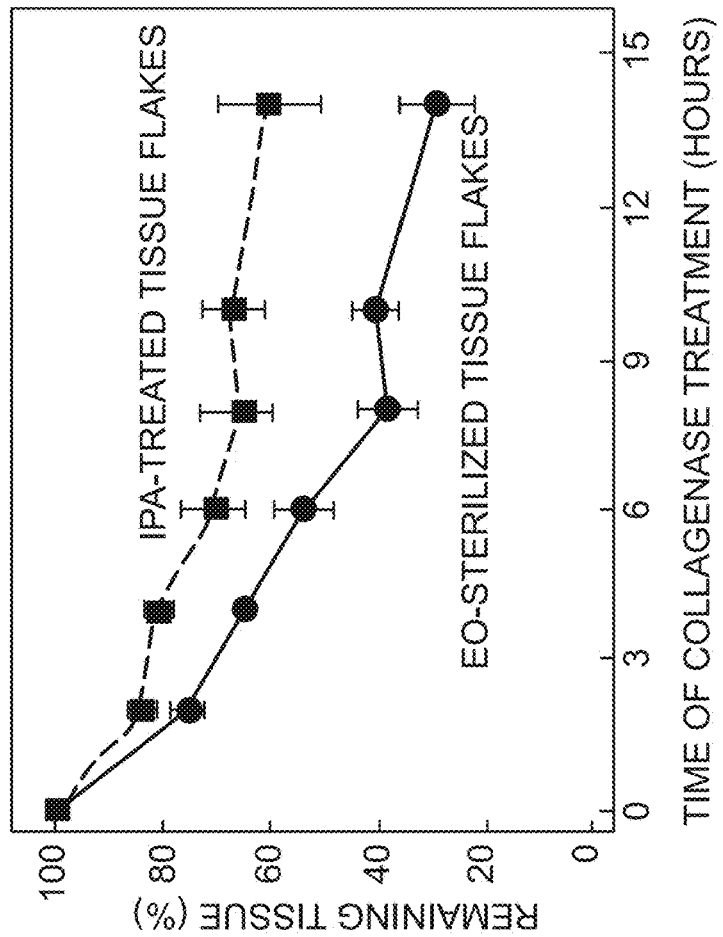

The susceptibility of processed, freeze-dried tissue flakes to enzyme degradation was tested with collagenase and trypsin assays. FIGS. 8A and 8B show the resistance of processed tissue material to collagenase and trypsin digestion, respectively. IPA-disinfected tissue flakes resisted collagenase and trypsin digestion fairly well. EO-sterilized material had increased susceptibility to proteolysis compared to the IPA-disinfected material.

Example 5

Suitability of Tissue Flakes to Permit Fluid Flow and Pressure Transduction

Figure 9B:
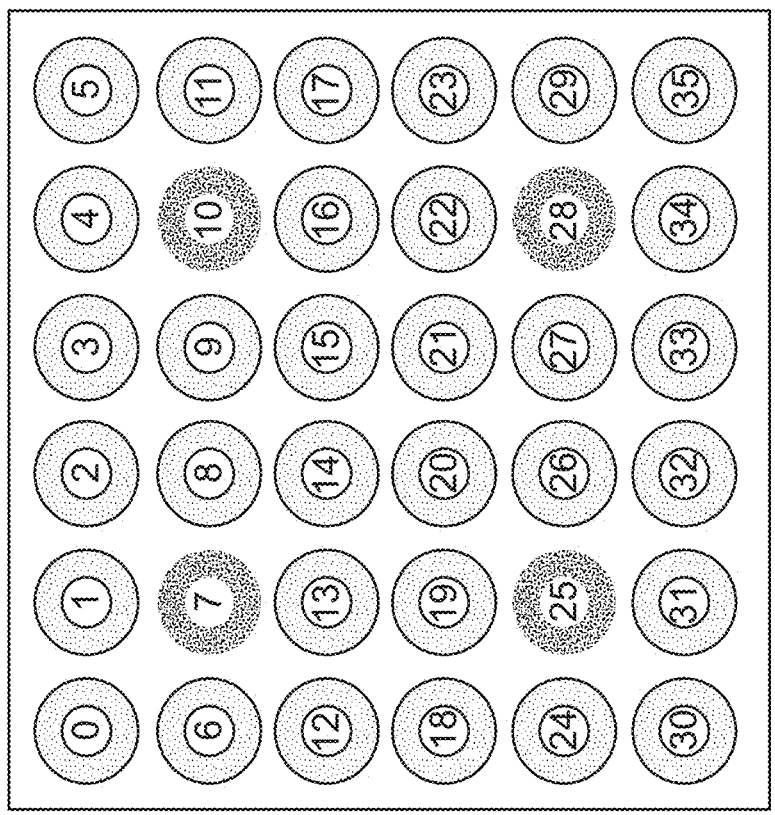
FIG. 9B is a schematic of a pressure testing pad, as described in Example 5.
Figure 9A:
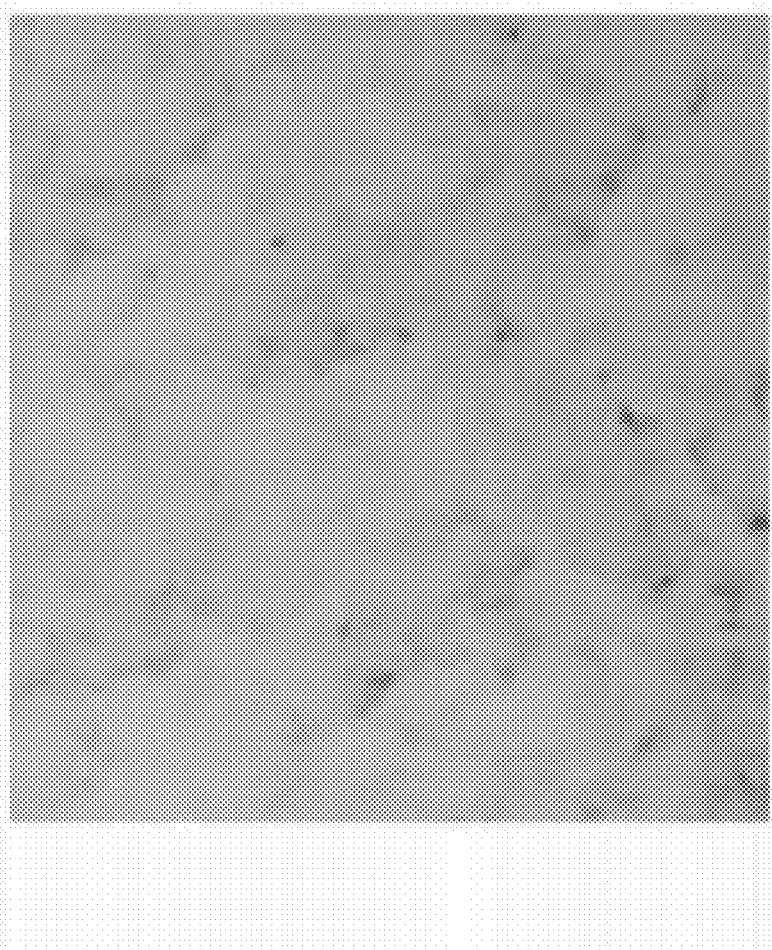
FIG. 9A is a photograph of rehydrated tissue flakes, according to certain embodiments

Upon rehydration, tissue flakes form a stable suspension without gelling or phase separation, allowing the tissue flakes to be used for filling large voids or defects (tens to hundreds of milliliters). The suspension of tissue flakes contains large, inter-connected channels that permit fluid to flow freely, and thus aid cell repopulation and revascularization when the flakes are used as tissue fillers. The ability of the tissue flake suspension to permit the flow of fluids and the transduction of pressure differentials was investigated. Rehydrated tissue flakes were placed onto Organza mesh and spread out over a 3"×3" pressure distribution pad with 36 sensor ports, as shown in FIGS. 9A and 9B. A piece of GranuFoam™ (3"×3", and 1.5" thick) was placed on the top of the tissue flake material and a 6"×6" V.A.C.® was attached to the dressing assembly along with a T.R.A.C.® pad. The assembly was connected to the V.A.C.® ATS therapy unit to produce a continuous pressure at 125 mm Hg. After 5 minutes of equilibrium, the negative pressure detected at the 36 ports was noted. Thereafter, 4 of the ports were disconnected from the pressure sensors and connected to a reservoir of dyed 0.9% saline solution for infusion at a rate of 500 mL per day via a peristaltic pump. The pressure at the 32 remaining ports was then monitored over time. The average pressure detected was approximately 110-112 mm Hg. The negative pressure was 111.4±0.9 (mean±SD), 110.1±1.4, and 110.6±1.3 mm Hg after 1, 2, and 3 hours respectively. The consistency indicated that pressure was distributed evenly across the entire dressing assembly, and the inter-connected channels were able to transduce pressure differentials well.

Example 6

Reconstructive Tissue Foam Made from Flake-Like Tissue Material

Figure 10B:
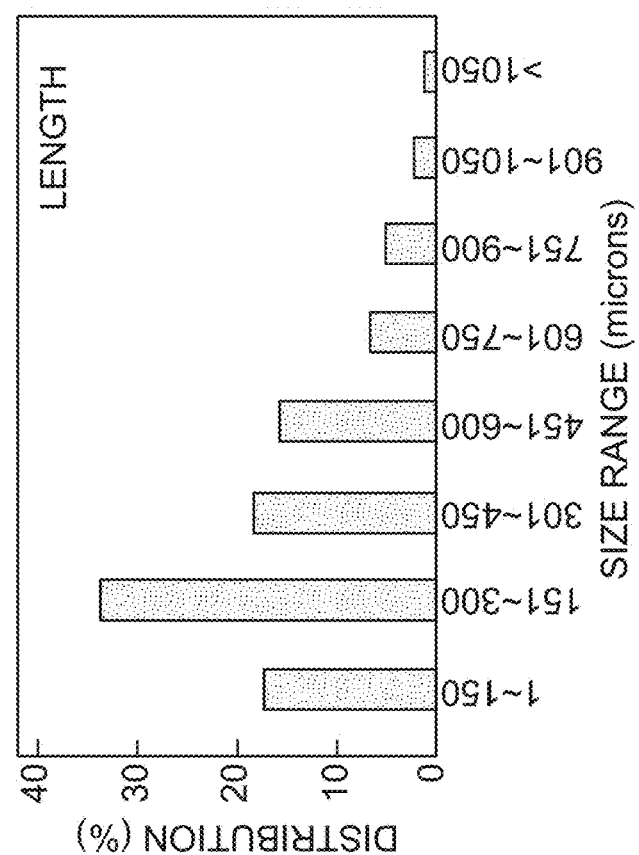
FIGS. 10A and 10B are charts showing the width and length size distribution, respectively, of processed tissue material, according to certain embodiments, as described in Example 6.
Figure 10A:
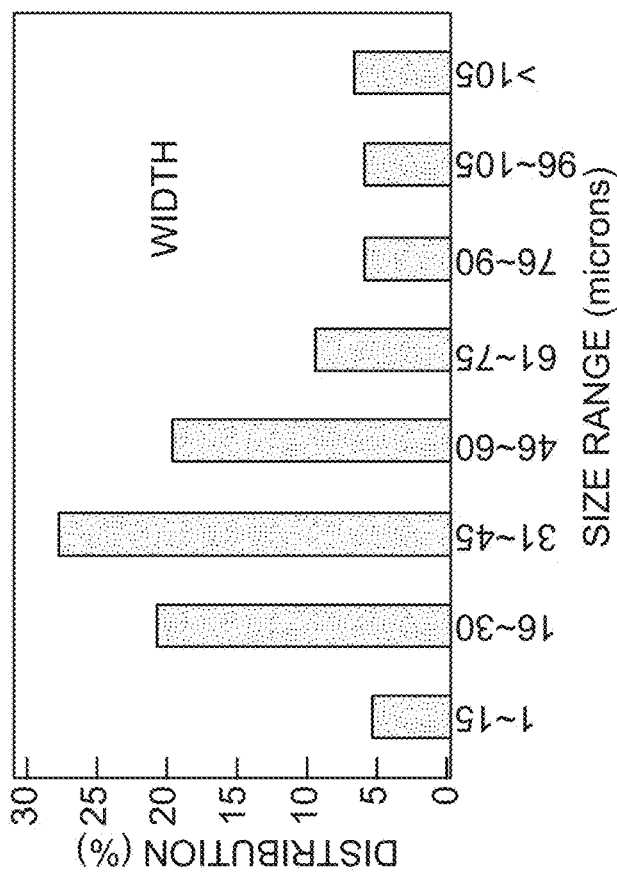

An acellular tissue matrix derived from porcine dermis was frozen at −80° C. and used to make tissue flakes aseptically with a medium size MICROPLANE® cheese grater. Approximately 50 g of tissue sample was suspended in 200 mL sterile water and then mixed using a RETSCH® blender at 4000 rpm in one minute intervals for a total of 5 cycles. As shown in FIGS. 10A and 10B, blending reduced the size of the tissue flake material. Blending the tissue flakes also resulted in a stable and consistent tissue suspension. The tissue suspension was distributed in 80 cm² plastic petri dishes at 25 mL suspension per dish and freeze-dried aseptically. The freeze-drying process included the controlled cooling of the tissue suspension from room temperature to −30° C. within 60 minutes and drying at a chamber pressure of 100 mT and a shelf temperature of 20° C. for 24 hours.

Figure 11B:
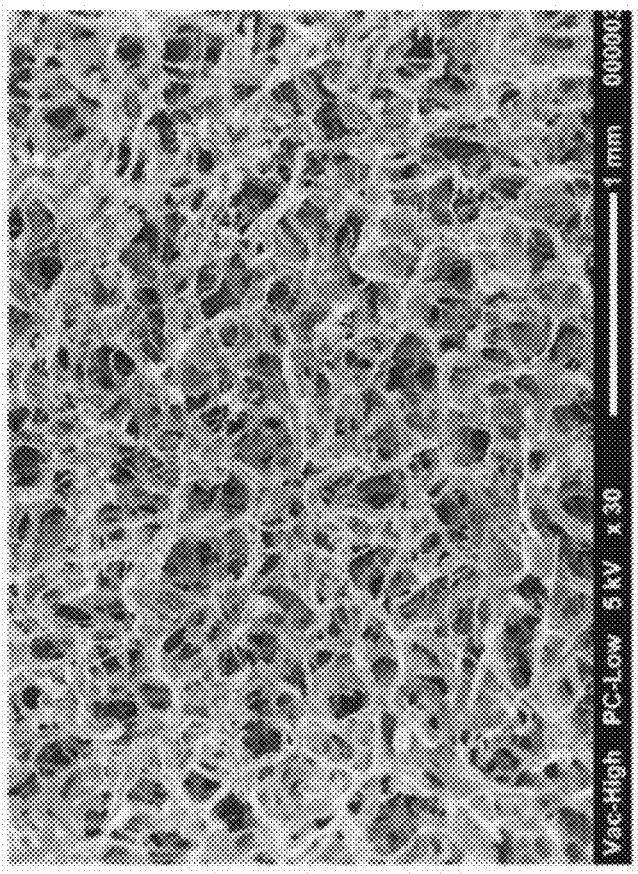
FIGS. 11A through 11D are photographs of a soft tissue foam, prepared according to certain embodiments, as described in Example 6.
Figure 11A:
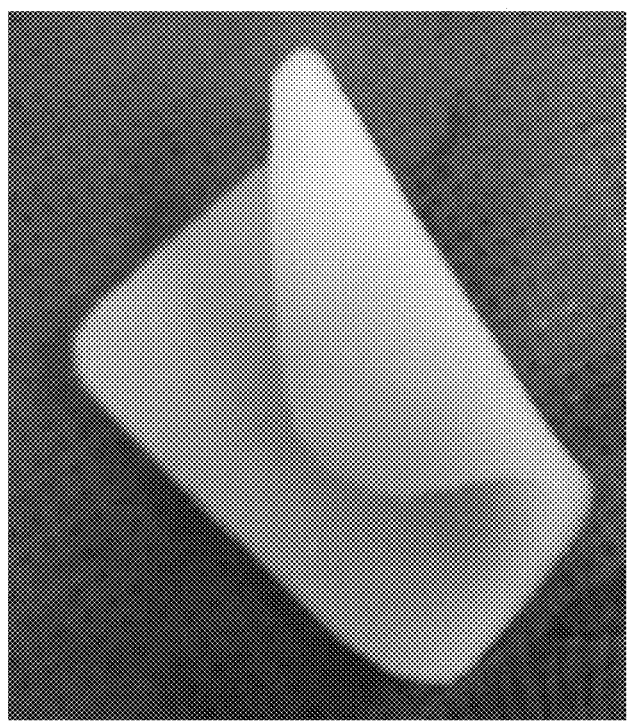
Figure 11D:
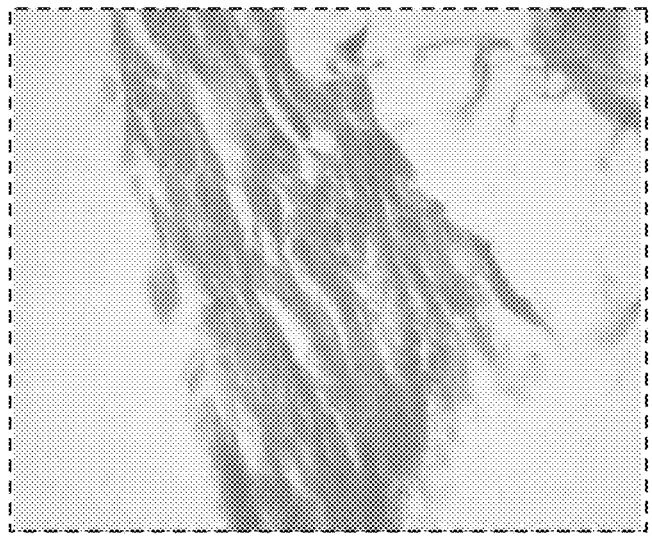
Figure 11C:
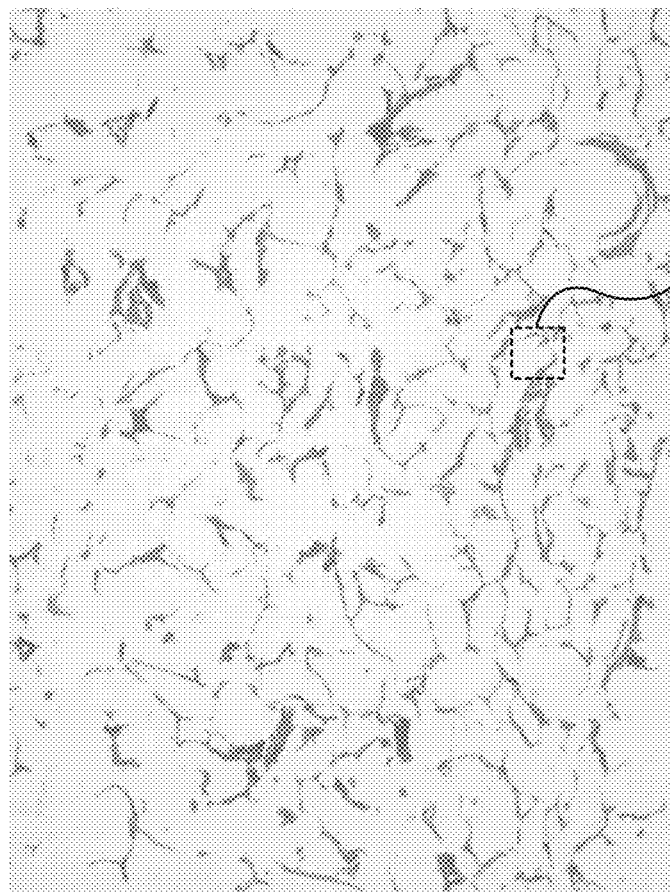

The process of blending and freeze-drying resulted in small tissue pieces of various dimensions intertwined and interlocked with one another, forming a soft tissue foam with interconnected macropores and preserved extracellular tissue matrix structures, as shown in FIGS. 11A through 11D. FIG. 11A presents a gross appearance of the tissue foam. FIG. 11B shows the interconnected macropores of the soft tissue foam under SEM microscopy. FIG. 11C is a histogram of the extracellular matrix structure of the foam using a hematoxylin and eosin stain. FIG. 11D is an enlarged view of a section found within FIG. 11C. As shown in FIGS. 11C and 11D, the tissue matrix of the foam has a fibrous, filamentous nature after blending and freeze-drying. The aseptically freeze-dried foam had a dry tissue mass of 9.9±0.3% (w/v, N=5).

Some of the freeze-dried tissue material was further treated at −100° C. under vacuum for 24 hours to increase the strength of the tissue foam. calorimetric measurement detected an onset denaturation temperature of 62.2±0.1° C. and a denaturation enthalpy of 60.5 J/g tissue mass, indicating no tissue collagen denaturation.

Figure 12A:
FIGS. 12A through 12D show various histological sections of various tissue matrices after implantation into an animal, according to certain embodiments, as described in Example 6.
Figure 12B:
Figure 12D:
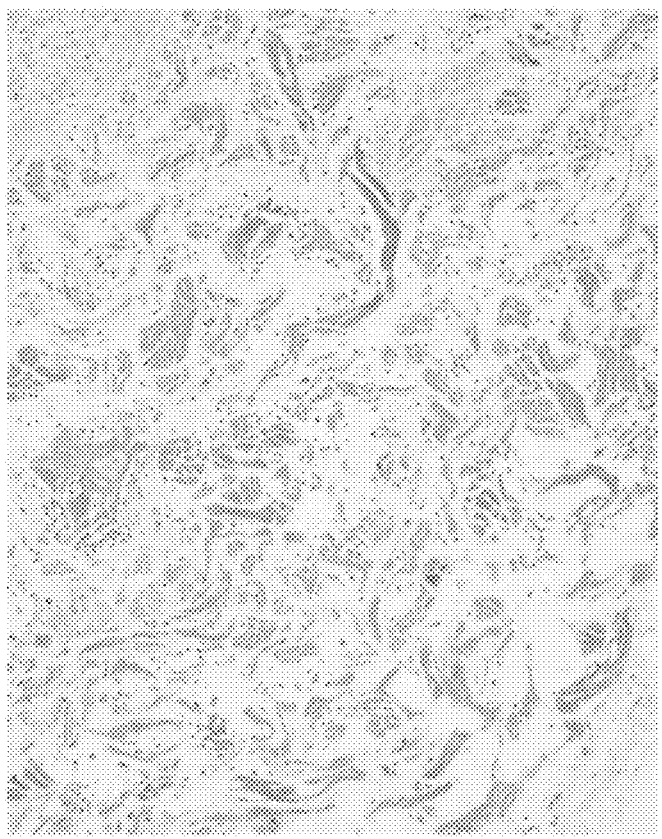
Figure 12C:
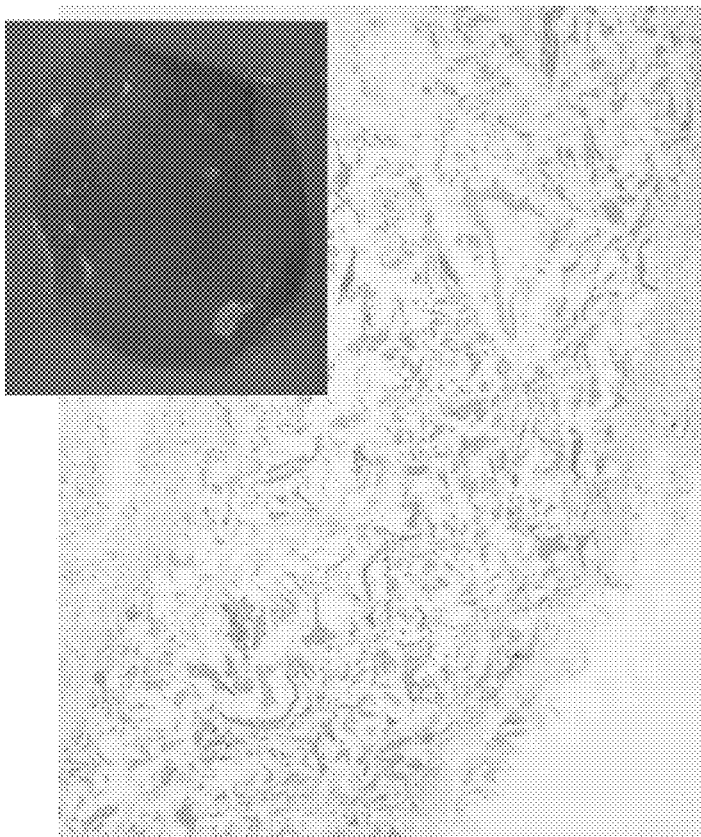

In a separate experiment using the freeze-dried material, the in vivo response of reconstructive tissue foam made from flake-like tissue material was investigated using an athymic rat model (*Rattus norvegicus*, nude rat). Tissue specimens (10 mm×10 mm, and ~3 mm thick) were prepared from the tissue foam and rehydrated in 0.9% saline solution. After rehydration, the tissue specimens were then implanted subcutaneously in athymic rats. For each rat, four separate incisions were made on the right and left side of the back through the skin and parallel to the lumbar region of the vertebral column. Pockets were formed by blunt dissection in the subcutaneous tissue in which the tissue material was introduced. Two specimens were implanted on the right side of the vertebral column and two specimens were implanted on the right, with the skin closed thereafter. Animals were euthanized either four or eight weeks after implantation. Implanted specimens with attached adjacent soft tissue were excised and the excised tissue samples were fixated in 10% formalin and processed for histological evaluation using hematoxylin and eosin stains. Histological slides were assessed microscopically for evidence of host cell repopulation and re-vascularization. As shown in FIG. 12, significant cell repopulation and revascularization were observed in 4-week implants (FIGS. 12A and 12B), while implanted tissue foams were fully repopulated in 8-weeks (FIGS. 12C and D). Inflammation was observed to be mild in 4-week explants, and subdued in 8-week explants.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A tissue matrix composition comprising:
    a group of small, irregularly sized and flake-shaped grated tissue matrix fragments intertwined and interlocked with one another to form a foam with interconnected macropores able to transduce pressure, wherein the group of flake-shaped tissue matrix fragments has a size distribution ranging from 0.2-5 mm in length, 0.2-3 mm in width, and 0.02-0.3 mm in thickness.

2. The composition of claim 1, wherein the tissue matrix fragments comprise acellular tissue matrix.

3. The composition of claim 2, wherein the acellular tissue matrix comprises an acellular dermal matrix.

4. The composition of claim 2, wherein the acellular tissue matrix comprises an acellular porcine dermal matrix.

5. The composition of claim 1, wherein the tissue matrix fragments are created using a process comprising freezing the tissue matrix prior to cutting grating.

6. The composition of claim 5, wherein the tissue matrix fragments are created using a process comprising applying a cryoprotectant solution prior to freezing.

7. The composition of claim 6, wherein the cryoprotectant solution comprises at least one of a maltodextrin, sucrose, polyethylene glycol (PEG), or polyvinylpyrrolidone (PVP) solution, or a combination thereof.

8. The composition of claim 7, wherein the cryoprotectant solution comprises a maltodextrin solution.

9. The composition of claim 8, wherein the maltodextrin solution comprises 5-50% (w/v) maltodextrin.

10. The composition of claim 8, wherein the maltodextrin solution comprises 15-25% (w/v) maltodextrin.

11. The composition of claim 1, wherein the tissue matrix is grated with a grater.

12. The composition of claim 1, wherein the tissue matrix is grated with a grating wheel.

13. The composition of claim 1, wherein the group of tissue matrix fragments have been sterilized by application of at least one of ethylene oxide, propylene oxide, gamma irradiation or e-beam irradiation.

14. The composition of claim 1, further comprising a bioactive substance.

15. The composition of claim 14, wherein the bioactive substance comprises an antimicrobial agent.

16. The composition of claim 14, wherein the bioactive substance comprises a cytokine.

17. The composition of claim 14, wherein the bioactive substance comprises a growth factor.

18. The composition of claim 14, wherein the bioactive substance comprises non-collagenous tissue.

19. The composition of claim 18, wherein the non-collagenous tissue comprises adipose tissue.

20. The composition of claim 14, wherein the bioactive substance comprises cells.

21. The composition of claim 20, wherein the cells comprise stem cells.

22. The composition of claim 1, wherein the group of flake-shaped tissue matrix fragments have been formed into the foam by placing the fragment in a liquid to form a stable suspension without gelling or phase separation of interconnected irregularly shaped particles and drying the suspension.

23. The composition of claim 22, wherein drying the suspension comprises freeze-drying the suspension.

* * * * *